(12) United States Patent
Kuppinger et al.

(10) Patent No.: US 8,481,784 B2
(45) Date of Patent: *Jul. 9, 2013

(54) SUPERABSORBENT POLYMERS AND METHODS OF MAKING THE SAME

(71) Applicant: Evonik Stockhausen GmbH, Krefeld (DE)

(72) Inventors: Franz-Felix Kuppinger, Marl (DE); Axel Hengstermann, Senden (DE); Guido Stochniol, Haltern am See (DE); Gunther Bub, Marl (DE); Jurgen Mosler, Marl (DE); Andreas Sabbagh, Bensheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/630,302

(22) Filed: Sep. 28, 2012

(65) Prior Publication Data

US 2013/0053522 A1    Feb. 28, 2013

Related U.S. Application Data

(63) Continuation of application No. 13/474,981, filed on May 18, 2012, now Pat. No. 8,293,941, which is a continuation of application No. 12/438,295, filed as application No. PCT/EP2007/058744 on Aug. 22, 2007, now Pat. No. 8,198,481.

(30) Foreign Application Priority Data

Aug. 22, 2006    (DE) .......................... 10 2006 039 203

(51) Int. Cl.
*C07C 51/42* (2006.01)

(52) U.S. Cl.
USPC ............ 562/600; 562/512; 562/598; 562/599

(58) Field of Classification Search
None
See application file for complete search history.

(56) References Cited

U.S. PATENT DOCUMENTS

| | | | |
|---|---|---|---|
| 5,079,164 A | 1/1992 | Kirkovits et al. | |
| 5,387,720 A | 2/1995 | Neher et al. | |
| 5,510,526 A | 4/1996 | Baniel et al. | |
| 5,543,546 A | 8/1996 | Tsuneki et al. | |
| 6,013,494 A | 1/2000 | Nakamura et al. | |
| 6,107,494 A | 8/2000 | Lee et al. | |
| 6,136,576 A | 10/2000 | Diaz-Torres et al. | |
| 6,187,951 B1 | 2/2001 | Baniel et al. | |
| 6,448,439 B1 | 9/2002 | Eck et al. | |
| 6,664,419 B1 | 12/2003 | Bub | |
| 7,186,856 B2 | 3/2007 | Meng et al. | |
| 7,294,741 B2 | 11/2007 | Bub et al. | |
| 7,557,245 B2 | 7/2009 | Nordhoff et al. | |
| 7,557,246 B2 | 7/2009 | Nordhoff et al. | |
| 7,803,969 B2 | 9/2010 | Nordhoff et al. | |
| 7,939,597 B2 | 5/2011 | Bub et al. | |
| 7,964,689 B2 | 6/2011 | Nordhoff et al. | |
| 8,178,717 B2 | 5/2012 | Balduf et al. | |
| 8,198,481 B2 * | 6/2012 | Kuppinger et al. ........... 562/600 |
| 2003/0018214 A1 | 1/2003 | Decker et al. | |
| 2004/0116741 A1 | 6/2004 | Nordhoff et al. | |
| 2006/0013748 A1 | 1/2006 | Nordhoff et al. | |
| 2008/0091048 A1 | 4/2008 | Nordhoff et al. | |
| 2009/0023006 A1 | 1/2009 | Bub et al. | |
| 2009/0068440 A1 | 3/2009 | Bub et al. | |
| 2009/0149562 A1 | 6/2009 | Nordhoff et al. | |
| 2011/0046297 A1 | 2/2011 | Hengstermann et al. | |
| 2011/0144294 A1 | 6/2011 | Bub et al. | |
| 2011/0166304 A1 | 7/2011 | Zanthoff et al. | |
| 2011/0275777 A1 | 11/2011 | Stochniol et al. | |
| 2012/0226003 A1 | 9/2012 | Balduf et al. | |

FOREIGN PATENT DOCUMENTS

| | | |
|---|---|---|
| DE | 4000942 C2 | 1/1992 |
| DE | 4238493 C1 | 4/1994 |
| DE | 10149353 A1 | 7/2002 |
| DE | 69431928 T2 | 11/2003 |
| EP | 1669459 A1 | 6/2006 |
| GB | 1009370 | 11/1965 |
| WO | 9524496 A1 | 9/1995 |
| WO | 9914181 A1 | 3/1999 |
| WO | 0045928 A1 | 8/2000 |
| WO | 0116346 A1 | 3/2001 |
| WO | 0242418 A2 | 5/2002 |
| WO | 02090312 A1 | 11/2002 |
| WO | 03062173 A2 | 7/2003 |
| WO | 03082795 A2 | 10/2003 |
| WO | 2004076398 A1 | 9/2004 |
| WO | 2005003074 A1 | 1/2005 |
| WO | 2005073161 A1 | 8/2005 |

(Continued)

OTHER PUBLICATIONS

International Preliminary Report on Patentability mailed on Apr. 2, 2009 in PCT/EP2007/058744.

(Continued)

*Primary Examiner* — Sudhakar Katakam
(74) *Attorney, Agent, or Firm* — Smith Moore Leatherwood LLP; Philip P. McCann

(57) ABSTRACT

In one aspect, a process for the preparation of a superabsorbent polymer is described herein. In some embodiments, the process comprises (I) preparing acrylic acid, wherein the process comprises (a1) provision of a fluid F1 having a composition comprising from about 5 to about 20 wt. % of hydroxypropionic acid, salts thereof, or mixtures thereof; from about 0.1 to about 5 wt. % of inorganic salts; from about 0.1 to about 30 wt. % of organic compounds which differ from hydroxypropionic acid; from 0 to about 50 wt. % of solids; and from about 20 to about 90 wt. % of water; (a2) dehydration of said hydroxypropionic acid to give a fluid F2 containing acrylic acid; and (a3) purification of said fluid F2 to give a purified acrylic acid phase comprising acrylic acid having a purity of at least 70 wt. %; and (II) polymerizing the acrylic acid of (I) to form a superabsorbent polymer.

23 Claims, 5 Drawing Sheets

FOREIGN PATENT DOCUMENTS

| WO | 2005095320 A1 | 10/2005 |
|---|---|---|
| WO | 2006008083 A1 | 1/2006 |
| WO | 2006029821 A1 | 3/2006 |

OTHER PUBLICATIONS

International Search Report mailed on Dec. 21, 2007 in PCT/EP2007/058744.

B. Odell, G. Earlam, and D. Cole-Hamilton, "Hydrothermal Reactions of Lactic Acid Catalysed by Group VIII Metal Complexes," copyright 1985, Journal of Organometallic Chemistry, vol. 290, pp. 241-248.

A. Qatibi et al., "Anaerobic Degradation of Glycerol by Desulfovibrio fructosovorans and D. carbinolicus and Evidence for Glycerol-Dependent Utilization of 1,2-Propanediol," copyright 1998, Current Microbiology, vol. 36, pp. 283-290.

M. Sobolov and K.L. Smiley, "Metabolism of Glycerol by Acrolein-Forming Lactobacillus," copyright Jul. 1959, Journal of Bacteriology, vol. 79, pp. 261-266.

O. Wörz and H. Mayer, "Reaction Columns," copyright 1992, Ullmann's Encyclopedia of Industrial Chemistry, vol. B4, pp. 321-323.

* cited by examiner

Biomass

Acrylic acid

SUPERABSORBENT POLYMERS AND METHODS OF MAKING THE SAME

This application is a continuation of U.S. application Ser. No. 13/474,981 with a filing date of May 18, 2012, currently pending, which is a continuation of U.S. application Ser. No. 12/438,295 with a filing date of Nov. 12, 2009, now U.S. Pat. No. 8,198,481, which is a national stage application under 35 U.S.C. 371 of international application No. PCT/EP2007/058744 filed 22 Aug. 2007, and claims priority to German Application No. DE 10 2006 039 203.5-44 filed 22 Aug. 2006, the disclosures of which are expressly incorporated herein by reference.

BACKGROUND

The present invention relates to a process for the preparation of acrylic acid, a device for the preparation of acrylic acid, a process for the preparation of polyacrylates, a device for the preparation of polyacrylates, the use of acrylic acid, and acrylic acid, polyacrylates and chemical products containing these, in particular superabsorbers and diapers.

Acrylic acid is a starting compound of great technical importance. It serves inter alia for the preparation of polyacrylates, in particular crosslinked, partly neutralized polyacrylates which have a large capacity for absorption of water in the dry and substantially anhydrous state. This can make up more than ten times its own weight. Because of the high absorption capacity, absorbent polymers are suitable for incorporation into water-absorbing structures and objects, such as e.g. baby diapers, incontinence products or sanitary napkins These absorbent polymers are also called "superabsorbers" in the literature. In this connection, reference is made to "*Modern Superabsorbent Polymer Technology*"; F. L. Buchholz, A. T. Graham, Wiley-VCH, 1998.

Acrylic acid is conventionally obtained from propylene by a gas phase oxidation which proceeds in two stages, in which propylene is first oxidized to give acrolein, which is then reacted further to give acrylic acid. A disadvantage of this two-stage process for the preparation of acrylic acid is on the one hand that the temperatures used in the two reaction stages, which are conventionally between 300 and 450° C., lead to the formation of undesirable cracking products. This in turn results in an undesirably large amount of impurities being obtained, which may also be polymerizable and can be incorporated into the polymer backbone acid in the presence of crosslinking agents. This has an adverse effect on the properties of the superabsorbers. Aldehydes in particular, such as, for example, furfural, acrolein or benzaldehyde, furthermore act as inhibitors in the free radical polymerization, with the consequence that the polymers still contain considerable amounts of soluble constituents if they are not extracted from the acrylic acid employed for the polymerization by elaborate purification steps.

It is also to be noted that if superabsorbers are employed in hygiene articles and in products for wound treatment, the toxic acceptability requirement is very high. This means that the educts employed for the preparation of the superabsorbers likewise must have the highest possible purities. It is therefore of great importance to provide acrylic acid as the main educt in an inexpensive manner in a form which is as pure as possible for the preparation of superabsorbers.

A further disadvantage of the conventional process for the preparation of acrylic acid is that the educt employed (propylene) is prepared from crude oil and therefore from non-regenerating raw materials, which from economic aspects above all is a disadvantage in the long term above all in view of the increasingly more difficult and above all more expensive production of crude oil.

Here also, some approaches for counteracting this problem are already described in the prior art. It is thus known in particular to obtain acrylic acid starting from hydroxypropionic acids, for example from 2-hydroxypropionic acid or 3-hydroxypropionic acid, by dehydration of the hydroxypropionic acid.

The preparation of 2-hydroxypropionic acid by a fermentative route from biomass, such as glucose or molasses, and by a synthetic route is known inter alia from PEP Review 96-7 "*Lactic acid by Fermentation*" by Ronald Bray of June 1998.

WO-A-03/62173 describes the preparation of 3-hydroxypropionic acid, which can serve inter alia as a starting substance for acrylic acid synthesis. In this context, according to the teaching of WO-A-03/62173 α-alanine is first formed fermentatively from pyruvate, and is then converted into beta-alanine by means of the enzyme 2,3-aminomutase. The β-alanine in turn is converted via β-alanyl-CoA, acrylyl-CoA, 3-hydroxypropionyl-CoA or via malonic acid semialdehyde into 3-hydroxypropionic acid, from which acrylic acid is obtained after a dehydration.

WO-A-02/42418 describes a further route for the preparation of, for example, 3-hydroxypropionic acid from regenerating raw materials. In this context, pyruvate is first converted into lactate, from which lactyl-CoA is subsequently formed. The lactyl-CoA is then converted via acrylyl-CoA and 3-hydroxypropionyl-CoA into 3-hydroxypropionic acid. A further route for the preparation of 3-hydroxypropionic acid described in WO-A-02/42418 envisages the conversion of glucose via propionate, propionyl-CoA, acrylyl-CoA and 3-hydroxypropionyl-CoA. This publication also describes the conversion of pyruvate into 3-hydroxypropionic acid via acetyl-CoA and malonyl-CoA. The 3-hydroxypropionic acid obtained by the particular routes can be converted into acrylic acid by dehydration.

WO-A-01/16346 describes the fermentative preparation of 3-hydroxypropionic acid from glycerol, in which microorganism which express the dhaB gene from *Klebsiella pneumoniae* (a gene which codes for glycerol dehydratase) and a gene which codes for an aldehyde dehydrogenase are employed. 3-Hydroxypropionic acid is formed from glycerol via 3-hydroxypropionaldehyde in this manner, and can then be converted into acrylic acid by dehydration.

Regardless of the enzymatic route by which the hydroxypropionic acid is obtained by fermentation, after the fermentative process an aqueous composition is present which, in addition to the hydroxypropionic acid, still contains numerous by-products, such as, for example, cells, non-converted biomass, salts and metabolism products formed alongside the hydroxypropionic acid.

In order to use the hydroxypropionic acid as a starting material for the preparation of acrylic acid, it is advantageous first to concentrate and to purify this. In this context, in connection with the purification of 3-hydroxypropionic acid it is known from WO-A-02/090312 first to add ammonia to the fermentation solution for neutralization, in order to convert the 3-hydroxypropionic acid into its ammonium salt. The fermentation solution obtained in this way is subsequently brought into contact with a high-boiling organic extraction agent and the mixture is heated, ammonia and water being stripped off in vacuo and the free 3-hydroxypropionic acid formed being extracted into the organic phase. An organic phase containing 3-hydroxypropionic acid is obtained in this manner, from which the 3-hydroxypropionic acid can be re-extracted or in which, after addition of a suitable catalyst, the 3-hydroxypropionic acid can be converted into acrylic acid. The disadvantage of the "salt splitting" process described in WO-A-02/090312 is, inter alia, that on the one hand aqueous phase to be purified must contain the 3-hydroxypropionic acid in an amount of at least 25 wt. % in order to render possible an effective purification by the so-called "salt splitting process". Since such high 3-hydroxypropionic acid concentrations cannot be achieved in the fermentation processes currently known for the preparation of 3-hydroxypropionic acid, it is necessary first to concentrate the 3-hydroxypropionic acid concentration in the fermentation solution. This is conventionally effected by evaporating the water out of the fermentation solution. Further disadvantages of the purification process described in WO-A-02/090312 are that on the one hand this process envisages the addition of a high-boiling organic solvent to the fermentation solution, which must be separated off from the 3-hydroxypropionic acid in the further course of the process, and that on the other hand in the purification of 3-hydroxypropionic acid from fermentation solutions which include numerous organic by-products, these organic by-products are also at least partly extracted into the organic solvent. In this case it is necessary for the organic phase obtained in the salt splitting to be purified further in order to obtain 3-hydroxypropionic acid with a satisfactory purity.

In connection with the purification of 2-hydroxypropionic acid (=lactic acid) from aqueous solutions, it is known from WO-A-95/024496 that the aqueous solution is first combined by means of an extraction agent comprising a water-immiscible trialkylamine having a total of at least 18 carbons in the presence of carbon dioxide under a partial pressure of at least $345 \times 10^3$ pascal to form an aqueous and an organic phase, and the lactic acid, which is in the organic phase, is subsequently extracted from the organic phase, for example by means of water. Here also the disadvantage of the purification process is that in the case of a fermentation solution as the starting composition, not only the lactic acid but also other by-products are dissolved in the organic phase, so that no pure lactic acid solution is obtained in the re-extraction with water.

In the dehydration of hydroxypropionic acid to give acrylic acid, water is furthermore obtained. Even if quite concentrated hydroxypropionic acid solutions or even relatively pure hydroxypropionic acid are employed, purification of an aqueous mixture of acrylic acid, hydroxypropionic acid and optional by-products obtained during the dehydration must therefore be carried out.

WO-A-2004/76398 proposes a vacuum distillation with dodecanol as an addition for separation of a mixture of acrylic acid and 3-hydroxypropionic acid. However, this gentle process is disadvantageous because of the use of dodecanol.

The present invention was based on the object of mitigating or even overcoming in context the disadvantages emerging from the prior art.

In particular, the present invention was based on the object of providing a process for the preparation of acrylic acid from a fluid phase, preferably based on an aqueous fermentation solution, with which an acrylic acid which is as pure as possible or an aqueous acrylic acid which is as pure as possible can be obtained under conditions which are as gentle as possible and simple. It should be possible for this purification process to be carried out with the lowest possible or even without the addition of organic solvents.

The present invention was furthermore based on the object of providing a process for the preparation of acrylic acid and a process for the preparation of polyacrylate, which renders possible a preparation of acrylic acid, in particular from biomass, which is as gentle and simple as possible.

The present invention was also based on the object of providing devices for the preparation of acrylic acid and polymers thereof with which such processes can be carried out.

SUMMARY

The present invention includes various embodiments set forth in the claims and including the following as taken in context with the present invention:

A process according to the present invention wherein said hydroxypropionic acid is 3-hydroxypropionic acid.

A device for the preparation of acrylic acid according to the present invention comprising the following units and stages, wherein said units and stages are connected to one another by fluid-carrying lines:
  i) a synthesis unit for the preparation of hydroxypropionic acid,
  ii) a dehydration stage for conversion of the hydroxypropionic acid into acrylic acid, followed by
  iii) a crystallizing unit.

A device for the preparation of acrylic acid according to the present invention wherein the dehydration stage is constructed as a pressure reactor.

A device for the preparation of acrylic acid according to the present invention wherein said dehydration stage has at least two reactors R1 and R2 connected to one another by fluid-carrying lines, of which one of said reactors can be loaded with a pressure $\Pi 1$ and the other can be loaded with a pressure $\Pi 2$, the pressure $\Pi 2$ differing from the pressure $\Pi 1$.

A device for the preparation of acrylic acid according to the present invention wherein said crystallizing unit is a suspension crystallization or a layer crystallization device.

A device for the preparation of acrylic acid according to the present invention wherein the purification unit comprises the following constituents connected to one another by fluid-carrying lines:
  i) a first crystallization region connected to a first separating region via a first guide line,
  ii) said first separating region connected to at least one melting unit via a second guide line,
  iii) said at least one melting unit connected to a second crystallization region via a third guide line,
  iv) said second crystallization region connected to a second separating region via a fourth guide line,
  v) said second separating region connected to a third crystallization region via a fifth guide line,
  vi) said third crystallization region connected to a third separating region via a sixth guide line.

A device for the preparation of acrylic acid according to the present invention wherein said first separating region is connected to said dehydration stage by fluid-carrying lines.

A device for the preparation of acrylic acid according to the present invention comprising the device for the preparation of acrylic acid according to the present invention and a polymerization reactor for the polymerization of acrylic acid.

A process for the preparation of acrylic acid according to the present invention comprising the process steps:
  (a1) provision of a fluid F1 containing a hydroxypropionic acid, aqueous phase P1,
  (a2) dehydration of said hydroxypropionic acid to give a fluid F2 containing acrylic acid, aqueous phase P2,
  (a3) purification of said fluid F2 containing acrylic acid, said aqueous phase P2, by crystallization to give a purified phase.

A process for the preparation of acrylic acid according to the present invention wherein an acrylic acid obtained from a process according the present invention is polymerized.

An acrylic acid obtained by a process according to the present invention.

The polyacrylate obtained by a process according to the present invention.

The polyacrylate according to present invention wherein this said polyacrylate is a water-absorbing polymer.

An article selected from fibers, films, molding compositions, textile and leather auxiliaries, flocculating agents, coatings or lacquers, wherein said article is based on the acrylic acid produced by a process according to the present invention.

A method of using an acrylic acid produced by a process according to the present invention in or for the production of an article selected from the group consisting of fibers, films, molding compositions, textile and leather auxiliaries, flocculating agents, coatings or lacquers.

The process according to the present invention wherein said fluid F1 is aqueous, and has a composition comprising:
(C1-1) 1 to 40 wt. % of hydroxypropionic acid, salts thereof or mixtures thereof,
(C1-2) 0.1 to 5 wt. % of inorganic salts,
(C1-3) 0.1 to 30 wt. % of organic compounds which differ from hydroxypropionic acid,
(C1-4) 0 to 50 wt. % of solids, and
(C1-5) 20 to 90 wt. % of water,
wherein the sum of components (C1-1) to (C1-5) is 100 wt. %.

The process according to the present invention wherein said dehydration is carried out in at least two reactors, comprising the following process steps:
i) heating of said aqueous phase P1 in at least one first reactor R1 in the presence of a homogeneous or heterogeneous catalyst to give a first aqueous fluid F1-1 containing acrylic acid under a pressure $\Pi 1$;
ii) introduction of said fluid F1-1 into a further reactor R2;
iii) heating of said fluid F1-1 introduced into said reactor R2 in the presence of a catalyst under a pressure $\Pi 2$ to give a fluid F1-2,
wherein said pressure $\Pi 2$ and said pressure $\Pi 1$ are not equal.

The process according to the present invention wherein a first crystal phase containing:
i) at least 5 wt. % of acrylic acid,
ii) at least 40 wt. % of water, and
iii) at most 10 wt. % of hydroxypropionic acid
is obtained.

The device according to the present invention wherein said crystallizing unit is a suspension crystallization or a layer crystallization device.

Overall, the aim of designing the particular process procedure as efficiently and inexpensively as possible to give end products which are as pure as possible is to be pursued, wherein as far as possible regenerable raw materials are to be used as starting substances. A contribution is thus to be made towards the preparation of acrylic acid based on regenerating raw materials not only being more sustainable and ecologically more advantageous than the conventional petrochemical route for the preparation of acrylic acid, which usually proceeds via propylene, but also being of economic interest.

A contribution towards achieving the abovementioned objects is made according to the invention by the process for the preparation of acrylic acid, by the device for the preparation of acrylic acid, by the process for the preparation of polyacrylates, by the device for the preparation of polyacrylates, and by the acrylic acid, polyacrylates and chemical products containing these, in particular superabsorbers and diapers, as described in the particular main and secondary claims. Further embodiments and developments, each of which can be combined individually or as desired with one another, are the subject matter of the particular dependent claims.

FIGURES

The foregoing and other features, aspects, and advantages of the present invention will become better understood with regard to the following description, appended claims, and accompanying drawings where:

DETAILED DESCRIPTION

Figure 1:
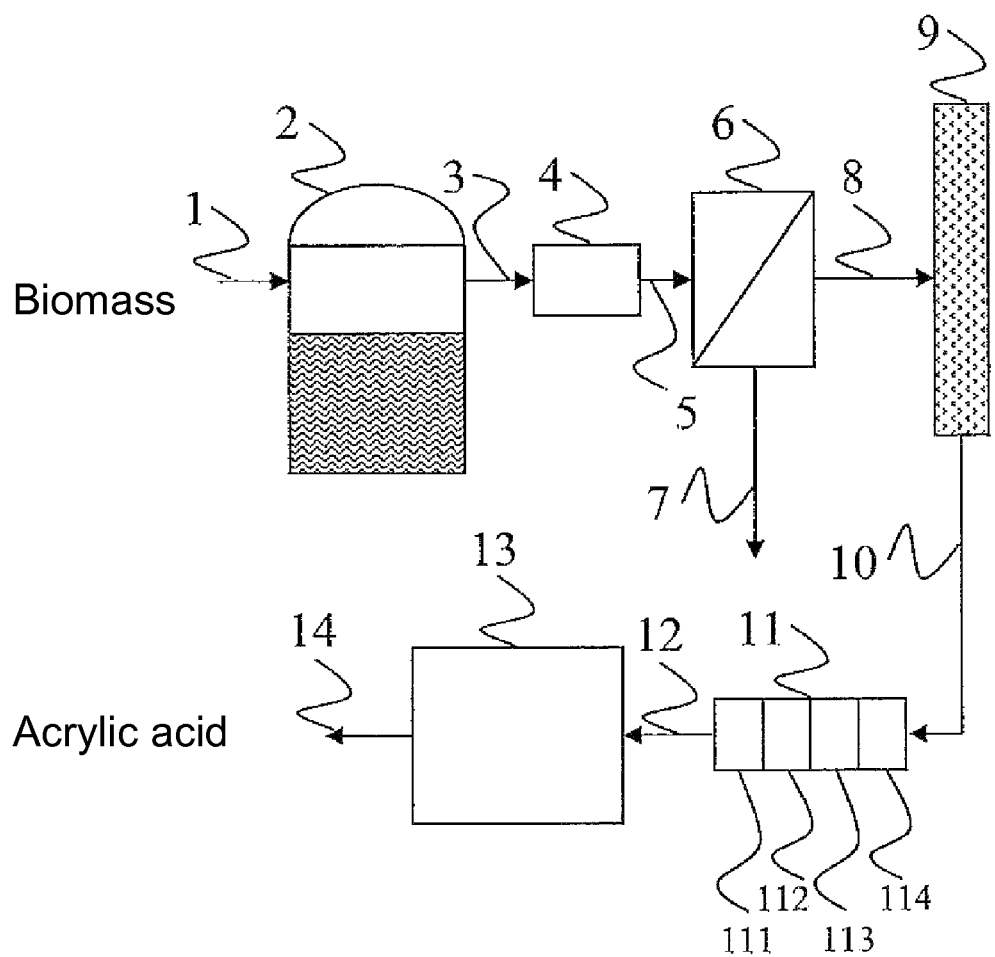
FIG. 1 is an illustration of the process flow according to the current invention.

The process according to the invention for the preparation of acrylic acid comprises the process steps:
(a1) provision of hydroxypropionic acid, preferably of 2-hydroxypropionic acid or 3-hydroxypropionic acid, most preferably of 3-hydroxypropionic acid, from a biological material, to give a fluid F1 containing hydroxypropionic acid, preferably 2-hydroxypropionic acid or 3-hydroxypropionic acid, most preferably 3-hydroxypropionic acid, in particular an aqueous phase P1,
(a2) dehydration of the hydroxypropionic acid, preferably the 2-hydroxypropionic acid or 3-hydroxypropionic acid, most preferably the 3-hydroxypropionic acid, to give a fluid F2 containing acrylic acid, in particular an aqueous phase P2,
(a3) purification of the fluid F2 containing acrylic acid, preferably the aqueous phase P2, by a suspension crystallization or a layer crystallization, to give a purified phase.

The terms "acrylic acid", "hydroxypropionic acid", "2-hydroxypropionic acid" and "3-hydroxypropionic acid" as used herein always describe in this context the corresponding carboxylic acid in that form in which they are present in the fluids F1 or F2 under the given pH conditions. The terms therefore always include the pure acid form (acrylic acid, hydroxypropionic acid, 2-hydroxypropionic acid or 3-hydroxypropionic acid), the pure base form (acrylate, hydroxypropionate, 2-hydroxypropionate or 3-hydroxypropionate) and mixtures of the protonated and deprotonated form of the acids.

In the process according to the invention it is preferable for at least one, preferably at least two of the steps of the process according to the invention to be carried out continuously and not to have to be constantly interrupted by batchwise reactions and started up again. Preferably, at least the steps of dehydration and of crystallization and particularly preferably all the steps are carried out continuously.

According to a particular embodiment of the preparation process according to the invention, the fluid F1 initially introduced in process step (a1) is an aqueous phase P1, this aqueous phase P1 preferably being obtained by a process comprising the process steps:
i) preparation, preferably fermentative preparation, of hydroxypropionic acid from a biological material, particularly preferably from carbohydrates, in particular from glucose, or from glycerol, in an aqueous composition to give an aqueous phase containing hydroxypropionic acid and microorganisms,
ii) optionally killing of the microorganisms, preferably by heating this aqueous phase to temperatures of at least 100° C., particularly preferably at least 110° C. and moreover preferably at least 120° C. for a duration of at least 60 seconds, for example 10 minutes and/or at least 30 minutes,
iii) optionally separating off of solids, in particular of microorganisms or unreacted biological material, from the aqueous phase, preferably by means of sedimentation, centrifugation or filtration.

Preferably, recombinant microorganisms, particularly preferably recombinant bacterial, fungal or yeast cells, are employed for the preferably fermentative preparation of the hydroxypropionic acid from a biological material in process step i). Recombinant microorganisms which are particularly preferred according to the invention are bacteria of the genera *Corynebacterium, Brevibacterium, Bacillus, Lactobacillus, Lactococcus, Candida, Pichia, Kluveromyces, Saccharomyces, Bacillus, Escherichia* and *Clostridium, Bacillus flavum, Bacillus lactofermentum, Escherichia coli, Saccharomyces cerevisiae, Kluveromyces lactis, Candida blankii, Candida rugosa, Corynebacterium glutamicum, Corynebacterium efficiens* and *Pichia postoris* being moreover preferred and *Corynebacterium glutamicum* being most preferred.

In this context, it is furthermore preferable according to the invention for the microorganisms to be genetically modified such that compared with their wild-type they show a formation of hydroxypropionic acid from a biological material, preferably from carbohydrates, such as glucose, or from glycerol, which is increased, preferably a formation which is increased by a factor of at least 2, particularly preferably of at least 10, moreover preferably of at least 100, moreover still more preferably of at least 1,000 and most preferably of at least 10,000. In this context, this increase in the hydroxypropionic acid formation can in principle be effected via all the metabolic pathways known to the person skilled in the art, in the case of the formation of 3-hydroxypropionic acid in particular via the routes described in the publications WO-A-03/62173, WO-A-02/42418 and WO-A-01/16346 and in the case of the formation of 2-hydroxypropionic acid in particular from bacteria strains of the genus *Bacillus* or *Lactobacillus*, for example in the manner described in DE 40 00 942 C2. The formation of hydroxypropionic acids, in particular of 2- or 3-hydroxypropionic acids, is particularly preferably carried out by means of recombinant microorganisms in which the activity of one or more enzymes relevant for the formation of the corresponding hydroxypropionic acids has been increased, it being possible for the increase in the enzyme activities to be effected by measures known to the person skilled in the art, in particular by mutation or increasing the gene expression.

The genetically modified microorganisms can be brought into contact with a suitable nutrient medium, and therefore cultured, continuously or discontinuously in the batch process (batch culturing) or in the fed batch process (feed process) or repeated fed batch process (repetitive feed process) for the purpose of the production of hydroxypropionic acid. A semi-continuous process such as is described in GB-A-1009370 is also conceivable. A summary of known culturing methods is described in the textbook by Chmiel ("*Bioprozesstechnik 1. Einführung in die Bioverfahrenstechnik [Bioprocess technology 1. Introduction to bioprocess technology]*" (Gustav Fischer Verlag, Stuttgart, 1991)) or in the textbook by Storhas ("*Bioreaktoren and periphere Einrichtungen [Bioreactors and peripheral equipment]*", Vieweg Verlag, Braunschweig/Wiesbaden, 1994).

The culture medium to be used must meet the requirements of the particular strains in a suitable manner. Descriptions of culture media of various microorganisms are contained in the handbook "*Manual of Methods for General Bacteriology*" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as biological material, in particular as a source of carbon. These substances can be used individually or as a mixture. The use of carbohydrates, in particular monosaccharides, oligosaccharides or polysaccharides, as is described in U.S. Pat. No. 6,013,494 and U.S. Pat. No. 6,136,576, of C5 sugars or of glycerol is particularly preferred.

Organic nitrogen-containing compounds, such as peptones, yeast extract, meat extract, malt extract, corn steep liquor, soybean flour and urea, or inorganic compounds, such as ammonium sulphate, ammonium chloride, ammonium phosphate, ammonium carbonate and ammonium nitrate, can be used as a source of nitrogen. The sources of nitrogen can be used individually or as a mixture.

Phosphoric acid, potassium dihydrogen phosphate or dipotassium hydrogen phosphate or the corresponding sodium-containing salts can be used as a source of phosphorus. The culture medium must furthermore contain salts of metals, such as e.g. magnesium sulphate or iron sulphate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a one-off batch or can be fed in during the culturing in a suitable manner.

Basic compounds, such as sodium hydroxide, sodium bicarbonate, potassium hydroxide, ammonia or aqueous ammonia, or acidic compounds, such as phosphoric acid or sulphuric acid, are employed in a suitable manner to control the pH of the culture, the addition of ammonia being particularly preferred. Antifoam agents, such as e.g. fatty acid polyglycol esters, can be employed to control the development of foam. Suitable substances having a selective action, such as e.g. antibiotics, can be added to the medium to maintain the stability of plasmids. Oxygen or oxygen-containing gas mixtures, such as e.g. air, are introduced into the culture in order to maintain aerobic conditions. The temperature of the culture is usually 20° C. to 45° C., and preferably 25° C. to 40° C.

In connection with this particular embodiment of the process according to the invention, it is preferable for the aqueous phase P1 prepared in process step (a1) to have a composition C1 comprising
(C1_1) 1 to 40 wt. %, preferably 5 to 30 wt. % and most preferably 10 to 20 wt. % of hydroxypropionic acid, preferably 2- or 3-hydroxypropionic acid and particularly preferably 3-hydroxypropionic acid, salts of these acids or mixtures thereof, (C1_2) 0.1 to 5 wt. %, preferably 0.3 to 2.5 wt. % and most preferably 0.5 to 1 wt. % of inorganic salts, (C1_3) 0.1 to 30 wt. %, preferably 0.5 to 20 wt. % and most preferably 1 to 10 wt. % of organic compounds which differ from the hydroxypropionic acid, (C1_4) 0 to 50 wt. %, preferably 1 to 40 wt. %, preferably 5 to 20 wt. % and most preferably 1 to 10 wt. % of solids, in particular solids of fine plant parts or cells and/or cell fragments, in particular of microorganisms or unreacted biological material, and (C1_5) 20 to 90 wt. %, preferably 30 to 80 wt. % and most preferably 40 to 70 wt. % of water, wherein the sum of components (C1_1) to (C1_5) is 100 wt. %.

This fluid phase preferably has a pH in a range of from 5 to 8, preferably 5.2 to 7 and particularly preferably 5.5 to 6.5.

The salt of the hydroxypropionic acid is preferably the sodium salt, the potassium salt, the calcium salt, the ammonium salt or mixtures thereof, the ammonium salt being particularly preferred.

The inorganic salts are preferably chosen from the group containing sodium chloride, potassium chloride, phosphates, such as sodium phosphate, sodium carbonate, sodium bicarbonate, sodium dihydrogen phosphate or disodium hydrogen phosphate, magnesium sulphate, iron sulphate, calcium chloride, calcium sulphate or ammonium salts, such as ammonium sulphate, ammonium chloride, ammonium phosphate, ammonium carbonate or ammonium nitrate.

The organic compounds which differ from the hydroxypropionic acid comprise, inter alia, unreacted biological material, such as, for example, carbohydrates or glycerol, metabolism products, such as, for example, lactate, pyruvate or ethanol, antibiotics, antifoam agents, organic buffer substances, such as, for example, HEPES, amino acids, vitamins, peptones, urea or nitrogen-containing compounds, such as are contained, for example, in yeast extract, meat extract, malt extract, corn steep liquor and soybean flour.

The aqueous fluid F1 obtained after the fermentation and containing hydroxypropionic acid and microorganisms or the aqueous phase P1 (=fermentation solution) can be heat treated in a further process step ii) in order to kill the microorganisms still contained therein. This is preferably effected by heating this aqueous phase P1 to temperatures of at least 100° C., particularly preferably at least 110° C. and moreover preferably at least 120° C. for a duration of at least 60 seconds, preferably at least 10 minutes and moreover preferably at least 30 minutes, the heating preferably being carried out in devices known for this to the person skilled in the art, such as, for example, an autoclave. Killing of the microorganisms by high-energy radiation, such as, for example, UV radiation, is also conceivable, killing of the microorganisms by heating being particularly preferred.

In this particular embodiment of the process according to the invention, it may furthermore be preferable for solids, in particular fine plant parts or cells and/or cell fragments, in particular microorganisms or unreacted biological material, to be separated off from the aqueous phase P1 obtained after the fermentation in a further process step iii) before, during or after the killing of the microorganisms in process step ii), it being possible for this separating off to be carried out by all the processes known to the person skilled in the art for separating off solids from liquid compositions, but preferably by sedimentation, centrifugation or filtration, separating off by filtration being most preferred. In this context, all the filtration processes which are mentioned in chapter 4.1.3 "Filtrieren and Auspressen [Filtration and pressing off]" in "Grundoperationen Chemischer Verfahrenstechnik [Basic operations of chemical process technology]", Wilhelm R. A. Vauck and Hermann A. Müller, WILEY-VCH-Verlag, 11th revised and extended edition, 2000, and seem suitable to the person skilled in the art for separating off solids, in particular microorganisms, from fermentation solutions can be used.

Before the fermentation solution obtained in this manner and optionally freed from solids is subjected to process step (a2) as the aqueous phase P1, it may also be appropriate to reduce the water content of this aqueous phase, in particular by a factor of less than 0.8, in particular less than 0.5, for example less than 0.3, by means of evaporation or distillation, reverse osmosis, electroosmosis, azeotropic distillation, electrodialysis or multiple phase separation. In this context, a reduction by a factor of less than 0.8 means that after the reduction the water content of the fermentation solution is less than 80% of the water content of the fermentation solution before the reduction.

In particular, it is preferable according to the invention for the water content to be reduced to the extent that the concentration of hydroxypropionic acid or of salts thereof in the fermentation solution is at least 10 wt. %, particularly preferably at least 20 wt. %, moreover preferably at least 30 wt. % and most preferably at least 40 wt. %.

In a modification of the invention, the process for the preparation of the fluid F1 or of the aqueous phase P1 furthermore comprises the process step (iv), in which at least a part of the water in the fermentation solution is separated off, this separating off preferably being carried out by the formation of a first phase and a second phase from the fluid F1, in particular from the aqueous phase P1. However, in the context of the process according to the invention it may be necessary for yet a further purification to be advantageous as process step iv), instead of or in addition to a separating off of solids iii). All the measures which are known to the person skilled in the art for this purpose and seem suitable are in principle possible as purifications. This is preferably chosen from a group consisting of salt precipitation, esterification, membrane and sorption processes or a combination of two. Of the membrane processes, micro-, ultra- or nanofiltration, osmosis, in particular reverse osmosis, or electrodialysis, or a combination of at least two of these are preferred. Preferred sorption processes are ion exchange, chromatography or extraction, preferably reactive extraction, or a combination of at least two of these. In the case of extraction, the use of hypercritical fluids, for example of $CO_2$, often in the presence of amines, is known. It is furthermore preferable for this formation of the first and second phase to be carried out by at least one or also at least two or more of the following separation processes:

evaporation or distillation,
reverse osmosis,
electroosmosis,
azeotropic distillation,
electrodialysis,
multiple phase separation, wherein the first and the second phase have different concentrations of acrylic acid, and after the formation of these two phases the phases are separated from one another to give a purified phase containing acrylic acid.

Process step (iv) can in principle be carried out before process step (a2) or, such as, for example, in the reactive distillation described below, at the same time as process step (a2). By process step (iv), a prepurified first or second phase is formed from the fluid F1, which is then subjected to the dehydration reaction in process step (a2).

All the devices which are mentioned in chapter 10.1 "Verdampfen [Evaporation]" in "Grundoperationen Chemischer Verfahrenstechnik [Basic operations of chemical process technology]", Wilhelm R. A. Vauck and Hermann A. Müller, WILEY-VCH-Verlag, 11th revised and extended edition, 2000, and seem suitable to the person skilled in the art for evaporation of water from a fermentation solution freed from solids can be employed as the evaporation device.

Reverse osmosis—also called hyperfiltration—is a pressure filtration on a semipermeable membrane in which, in particular, a pressure is used in order to reverse the natural osmosis process. In this context, the pressure to be applied must be greater than the pressure which would arise due to the osmotic requirement for balancing the concentration. The osmotic membrane, which allows through only the carrier liquid (solvent) and retains the dissolved substances (solutes), must be designed to withstand this often high pressure. When the pressure difference more than compensates the osmotic gradient, the solvent molecules pass through the membrane, as in a filter, while the impurity molecules are retained. The osmotic pressure increases with increasing concentration difference, and stops when the natural osmotic pressure is equal to the preset pressure. In a continuous procedure, the concentrate is removed continuously. Flow-through membranes can be used. In this context, the fluid F1 is pressed against a pore membrane, preferably of cellulose acetate or polyamide, under pressures of as a rule 2 to 15 MPa, water, but not the hydroxypropionic acid or salt thereof, being able to pass through the pores of the membrane. Suitable membrane materials and devices can be found, inter alia, in chapter 10.7 "Permeation" in "Grundoperationen Chemischer Verfahrenstechnik [Basic operations of chemical process technology]", Wilhelm R. A. Vauck and Hermann A. Müller, WILEY-VCH-Verlag, 11th revised and extended edition, 2000.

In electroosmosis, the electroosmotic pressure, with which a separation of the hydroxypropionic acid from an impurity, such as e.g. water, can likewise take place, is established in an equilibrium state. In electroosmosis, water is likewise separated off selectively from an aqueous composition via a semipermeable membrane, but in contrast to reverse osmosis the water is driven through the semipermeable membrane not via an increased pressure but by application of an electrical voltage of as a rule 6 to 20 V.

In azeotropic distillation or azeotropic rectification, an azeotropic mixture is separated by addition of a third component. Rectification is a thermal separation process and represents a further development of distillation or a succession of many distillation steps. The essential advantages of rectification are that the installation can be operated continuously and that the separating effect is many times higher compared with distillation, since the vapour is in contact with the liquid. As a result, the higher-boiling content condenses and the more readily volatile constituents of the liquid phase evaporate due to the heat of condensation liberated. The contact area between the vapour phase and liquid phase is provided by built-in components (e.g. bubble trays). As is also the case in distillation, under normal conditions only non-azeotropic mixtures can be separated. If it is necessary to separate an azeotropic mixture, the azeotropic point is shifted and should not lie in the concentration and temperature range of the installation. A shift is effected e.g. by changing the operating pressure or by addition of a particular auxiliary substance. Azeotropic distillation is carried out in particular using organic solvents, such as e.g. toluene or dodecanol, as an entraining agent which forms an azeotrope with water. The aqueous solution brought into contact with the organic solvent is subsequently distilled, water and the organic solvent being separated off from the composition.

Electrodialysis is understood as meaning splitting of a chemical compound under the action of an electrical current. In electrodialysis, two electrodes are immersed in the aqueous phase, formation of hydrogen occurring at the cathode and formation of oxygen occurring at the anode. Two phases are likewise formed in this manner, namely the aqueous phase freed from at least a part of the water, and the gas phase comprising hydrogen and oxygen. In this case in particular one of the components (e.g. water) containing the fluid phase is converted into its constituents, which can be removed as a gas or (e.g. by means of a precipitation reaction effected after the electrolytic reaction or a concentration of solid at an electrode) as a solid.

In multiple phase separation, such as is described, for example, in WO-A-02/090312, in a first process step the fluid F1, in particular the aqueous phase P1, in which the hydroxypropionic acid has preferably been at least partly converted into the ammonium salt by the addition of ammonia, is brought into contact with a high-boiling, preferably water-immiscible organic solvent or with a high-boiling solvent mixture. The composition which has been brought into contact with the high-boiling, preferably water-immiscible organic solvent or with a high-boiling solvent mixture is subsequently heated to a temperature of from preferably 20 to 200° C., particularly preferably 40 to 120° C., ammonium and water vapour escaping from the composition, and the hydroxypropionic acid is extracted in the acid form into the high-boiling organic solvent or into the high-boiling solvent mixture and an organic phase containing hydroxypropionic acid is obtained. This process, which is also called "salt splitting", is described in WO-A-02/090312. The organic phase obtained in this manner can be employed as fluid F1 in process step (a2).

In this context, those solvents which are mentioned as preferred extraction agents in WO-A-02/090312 are employed as preferred organic solvents. Preferred high-boiling organic solvents in this context are organic amines, in particular trialkylamines having a total number of carbon atoms of at least 18 and a boiling point of at least 100° C., preferably at least 175° C., under atmospheric pressure, such as trioctylamine, tridecylamine or tridodecylamine, and solvent mixture of these trialkylamines and high-boiling carbon-oxygen compounds, such as, for example, alcohols, high-boiling phosphorus-oxygen compounds, such as phosphoric acid esters, high-boiling phosphine sulphides or high-boiling alkyl sulphides, "high-boiling" preferably meaning that these compounds have a boiling point of at least 175° C. under atmospheric pressure.

After the fluid F1, in particular the aqueous phase P1, containing the ammonium salt of the hydroxypropionic acid has been brought into contact with these solvents or solvent mixture in accordance with the procedure described in WO-A-02/090312, the composition obtained in this way is heated, water vapour and ammonia escaping. The release of these components, which are at least partly in gaseous form under the temperature conditions, can optionally be promoted by a reduced pressure. Finally, an organic phase which contains the hydroxypropionic acid in its acid form and which can then be employed as fluid F1 in process step (a2) is obtained. It is also conceivable to re-extract the hydroxypropionic acid with water and to subject the aqueous hydroxypropionic acid solution obtained in this way to process step (a2).

A multiple phase separation such as is described, for example, in WO-A-95/024496 is furthermore conceivable. According to this separation process, a hydroxycarboxylic acid solution in which the hydroxycarboxylic acid is present as hydroxypropionate due to the addition of basic compounds, such as, for example, sodium bicarbonate, is combined, optionally after a filtration and after the water has been evaporated off, by means of an extraction agent comprising a water-immiscible trialkylamine having a total of at least 18 carbons in the presence of carbon dioxide under a partial pressure of at least $345 \times 10^3$ pascal to form an aqueous and an organic phase, and the hydroxypropionic acid, which is in the organic phase, is subsequently extracted from the organic phase, for example by means of water. In this multiple phase separation process also, both the organic phase containing hydroxypropionic acid and the aqueous phase which contains hydroxypropionic acid and is obtained after a re-extraction with water can be subjected to process step (a2).

The dehydration of the hydroxypropionic acid and therefore the synthesis of acrylic acid in process step (a2) is preferably carried out by heating the aqueous fermentation solution, which optionally has been freed from microorganisms and has optionally been dewatered, or the organic or aqueous phase obtained by applying multiple phase separation, this heating particularly preferably being carried out in the presence of a catalyst.

Both acidic and alkaline catalysts are possible dehydration catalysts. Acidic catalysts are preferred in particular because of the low tendency towards oligomer formation. The dehydration catalyst can be employed both as a homogeneous and as a heterogeneous catalyst. If the dehydration catalyst is present as a heterogeneous catalyst, it is preferable for the dehydration catalyst to be in contact with a support x. All the solids which seem suitable to the person skilled in the art are possible as the support x. In this connection, it is preferable for these solids to have suitable pore volumes which are suitable for good binding and uptake of the dehydration catalyst. Total pore volumes according to DIN 66133 in a range of from 0.01 to 3 ml/g are furthermore preferred, and those in a range of from 0.1 to 1.5 ml/g are particularly preferred. It is additionally preferable for the solids suitable as the support x to have a surface area in the range of from 0.001 to 1,000 m$^2$/g, preferably in the range of from 0.005 to 450 m$^2$/g and moreover preferably in the range of from 0.01 to 300 m$^2$/g according to the BET test in accordance with DIN 66131. On the one hand bulk material which has an average particle diameter in the range of from 0.1 to 40 mm, preferably in the range of from 1 to 10 mm and moreover preferably in the range of from 1.5 to 5 mm can be employed as the support for the dehydration catalyst. The wall of the dehydration reactor can furthermore serve as the support. Moreover, the support can be acidic or basic per se, or an acidic or basic dehydration catalyst can be applied to an inert support. Application techniques which may be mentioned are, in particular, immersion or impregnation, or incorporation into a support matrix.

Suitable supports x, which can also have dehydration catalyst properties, are, in particular, natural or synthetic silicatic substances, such as, in particular, mordenite, montmorillonite, acidic zeolites, acidic aluminium oxides, γ-Al$_2$O$_3$, support substances, such as oxidic or silicatic substances, for example Al$_2$O$_3$, TiO$_2$, coated with mono-, di- or polybasic inorganic acids, in particular phosphoric acid, or acidic salts of inorganic acids; oxides and mixed oxides. such as, for example, gamma-Al$_2$O$_3$ and ZnO—Al$_2$O$_3$ mixed oxides of the heteropolyacids.

In one embodiment according to the invention, the support x comprises at least in part an oxidic compound. Such oxidic compounds should contain at least one of the elements from Si, Ti, Zr, Al and P or a combination of at least two of these. Such supports can also themselves act as the dehydration catalyst due to their acidic or basic properties. A preferred class of compounds acting both as a support as x and as a dehydration catalyst contains silicon-aluminium-phosphorus oxides. Preferred basic substances which function both as a dehydration catalyst and as a support x contain alkali metal, alkaline earth metal, lanthanum, lanthanoids or a combination of at least two of these in their oxidic form, such as, for example, Li$_2$O-, Na$_2$O-, K$_2$O-, Cs$_2$O-, MgO-, CaO-, SrO- or BaO- or La$_2$O$_3$-containing substances. Such acidic or basic dehydration catalysts are commercially obtainable both from Degussa AG and from Südchemie AG. Ion exchangers represent a further class. These can also be either in basic or in acidic form.

Possible homogeneous dehydration catalysts are, in particular, inorganic acids, preferably phosphorus-containing acids, and moreover preferably phosphoric acid. These inorganic acids can be immobilized on the support x by immersion or impregnation.

The use of heterogeneous catalysts has proved particularly suitable in gas phase dehydration in particular. In liquid phase dehydration, however, both homogeneous and heterogeneous dehydration catalysts are employed.

It is furthermore preferable for a dehydration catalyst having an H$_0$ value in the range of from +1 to −10, preferably in a range of from +2 to −8.2 and moreover preferably in the case of the liquid phase dehydration in a range of from +2 to −3 and in the gas phase dehydration in a range of from −3 to −8.2 bar to be employed in the process according to the invention for the preparation of acrylic acid. The H$_0$ value corresponds to the Hammett acidity function and can be determined by so-called amine titration and use of indicators or by absorption of a gaseous base—see "Studies in Surface Science and Catalytics", vol. 51, 1989: "New solid acids and bases, their catalytic properties", K. Tannabe et al. Further details on the preparation of acrolein from glycerol are furthermore to be found in DE 42 38 493 C1.

According to a particular embodiment of the process according to the invention for the preparation of acrylic acid, a porous support body which is preferably based to the extent of at least 90 wt. %, moreover preferably to the extent of at least 95 wt. % and most preferably to the extent of at least 99 wt. % on a silicon oxide, preferably on SiO$_2$, and has been brought into contact with an inorganic acid, preferably with phosphoric acid, or with super-acids, such as, for example, sulphated or phosphated zirconium oxide, is employed as an acidic solid catalyst. The porous support body is preferably brought into contact with the inorganic acid by impregnation of the support body with the acid, this preferably being brought into contact with the support body in an amount in a range of from 10 to 70 wt. %, particularly preferably in a range of 20 to 60 wt. % and moreover preferably in a range of from 30 to 50 wt. %, based on the weight of the support body, and then being dried. After the drying, the support body is heated for fixing of the inorganic acid, preferably to a temperature in a range of from 300 to 600° C., moreover preferably in a range of from 400 to 500° C.

According to a particular embodiment of the process according to the invention, the dehydration of the hydroxypropionic acid in process step (a2) is carried out by a liquid phase dehydration, most preferably by means of a so-called "reactive distillation".

"Reactive distillation" is a reaction from which one component is separated off by evaporation and the chemical equilibrium of this reaction is thereby influenced. In particular, simultaneous carrying out of a chemical reaction and a distillation in one column, in particular a countercurrent column, is called "reactive distillation". This simultaneous carrying out of the reaction and substance separation is particularly advantageous for those reactions in which the educts are not converted completely into the desired products due to the position of the chemical equilibrium. By the simultaneous separating off of the reaction products from the reaction space, an almost complete reaction also takes place in these cases in a single apparatus. Further advantages of reactive distillation are suppression of undesirable side reactions, thermal utilization of an exothermic heat of reaction for the distillation and facilitation of the subsequent working up of the product. In connection with the dehydration of hydroxypropionic acid, the term "reactive distillation" accordingly preferably describes a process in which the fluid F1 containing the hydroxypropionic acid, or the aqueous phase P1, which has been obtained in process step (a1), optionally after a further treatment by means of one or all of the process steps (i) to (iv), is heated in the presence of a dehydration-promoting catalyst under conditions under which the hydroxypropionic acid is at least partly converted into acrylic acid and under which at the same time water in the reaction solution can be distilled off. In this manner, the hydroxypropionic acid is dehydrated to give acrylic acid and the reaction mixture is distilled at the same time, water being separated off as the distillate and a bottom product containing acrylic acid being obtained.

In order to avoid decarboxylation reactions during the reactive distillation, it is furthermore particularly advantageous to carry out this reactive distillation in a $CO_2$ atmosphere. This furthermore has the advantage that the $CO_2$ is present in the aqueous reaction mixture at least partly in the form of carbonic acid, and as an acid at the same time promotes the dehydration reaction as a catalyst. In this context, the term "$CO_2$ atmosphere" is preferably understood as meaning an atmosphere which contains at least 10 vol. %, particularly preferably at least 25 vol. % and most preferably at least 50 vol. % of $CO_2$.

All the distillation or rectification devices known to the person skilled in the art can be employed as reactors for the reactive distillation. In this context, in the case of a heterogeneous catalysis the catalyst can be immobilized on a suitable support inside these distillation or rectification devices, for example by using structured packings, such as are obtainable, for example, under the name "Katapak-SP" from Sulzer-Chemtech, or by using thermal sheets coated with catalyst, and in the case of a homogeneous catalysis it can also be introduced into the inside of the distillation or rectification devices via a suitable inlet. Packed columns which contain packing bodies, such as, for example, hollow cylindrical packing materials, for example RASCHIG rings, INTOS rings, PALL rings, wire mesh rings, extended jacket rings, coiled rings, WILSON spiral rings or PYM rings, reel-shaped packing bodies, such as, for example, HALTMEIER rolls, saddle-shaped packing bodies, such as, for example, BERL saddles, INTALOX saddles or wire mesh saddles, cross-shaped packing bodies, such as, for example, twinned bodies, propeller bodies or star-shaped bodies, box-like packing bodies, such as, for example, HELI-PAK bodies or OCTA-PAK bodies, or spherical packing bodies, such as, for example, ENVI-PAK bodies, or plate columns can furthermore be employed in principle, it being possible for the packing bodies described above to be at least partly coated with catalyst. Packed columns have a very low liquid content compared with plate columns. This is indeed often advantageous for the rectification, since the risk of thermal decomposition of the substances is thereby reduced. However, the low liquid content of packed columns is a disadvantage for reactive distillation, especially in the case of reactions having a finite rate of reaction. In order to achieve the desired conversions in slow reactions, a long dwell time of the liquid in the apparatus must therefore be ensured. The use of plate columns can therefore be particularly advantageous according to the invention. These have a high liquid content, and indeed both in the two-phase layer on the plate and in the downcomers. Both portions of the liquid content can be modified in a targeted manner and adapted to the particular requirements of the reactive distillation by construction measures, i.e. by the design of the plates. The catalyst can furthermore be distributed over the entire length, that is to say from the bottom region to the top region, of the distillation or rectification devices. However, it is also conceivable for the catalyst to be located only in a particular region, preferably in the lower half, particularly preferably in the lower third and most preferably in the lower quarter of the distillation or rectification device.

In the case of the abovementioned reactive distillation, the process according to the invention preferably includes the following process steps:

(a1) preparation of hydroxypropionic acid, preferably of 2-hydroxypropionic acid or 3-hydroxypropionic acid, most preferably 3-hydroxypropionic acid, from a biological material, to give an aqueous phase P1 containing hydroxypropionic acid, preferably 2-hydroxypropionic acid or 3-hydroxypropionic acid, most preferably 3-hydroxypropionic acid, wherein the preparation of the aqueous phase P1 includes the following process steps:
 i) preparation, preferably fermentative preparation, of hydroxypropionic acid from a biological material, particularly preferably from carbohydrates, in particular from glucose, or from glycerol, in an aqueous composition to give an aqueous phase containing hydroxypropionic acid and microorganisms,
 ii) optionally killing of the microorganisms, preferably by heating this aqueous phase to temperatures of at least 100° C., particularly preferably at least 110° C. and moreover preferably at least 120° C. for a duration of at least 60 seconds, for example 10 minutes and/or at least 30 minutes, and
 iii) optionally separating off of solids, in particular of microorganisms or unreacted biological material, from the aqueous phase, preferably by means of sedimentation, centrifugation or filtration,
 iv) optionally at least partly separating off the water from the aqueous phase,
(a2) dehydration of the hydroxypropionic acid, preferably the 2-hydroxypropionic acid or 3-hydroxypropionic acid, most preferably the 3-hydroxypropionic acid, by means of a reactive distillation, preferably under a $CO_2$ atmosphere, to give a fluid F2 containing acrylic acid, in particular an aqueous phase P2, as the bottom product,
(a3) purification of the bottom product containing acrylic acid by a suspension crystallization or a layer crystallization, to give a purified phase.

In order to ensure the longest possible dwell time of the fluid F1 or of the aqueous phase P1 in the dehydration reactors, it may be advantageous to employ, in addition to the distillation or rectification device, at least one further reactor in which at least a part of the hydroxypropionic acid contained in the fluid F1 or in the aqueous phase P1 is converted into acrylic acid, before the fluid F1 or the aqueous phase P1 is introduced into the distillation or rectification device for further reaction.

In connection with the process according to the invention described above, especially if a reactive distillation is carried out, it is therefore particularly preferable for the dehydration to be carried out at least in two reactors, the second and optionally each further reactor being designed as a reactive distilling device. In this context, the aqueous phase P1—preferably freed from solids—is heated in at least one first reactor R1, which is preferably not constructed as a distillation or rectification device, in the presence of a homogeneous or heterogeneous catalyst, preferably an inorganic acid, particularly preferably phosphoric acid, to give a first aqueous fluid F1_1 containing acrylic acid, preferably a first aqueous phase P1_1 containing acrylic acid, this heating being carried out under a pressure $\Pi1$. This fluid F1_1 or this aqueous phase P1_1 is subsequently introduced into a further reactor R2, which likewise contains a homogeneous or heterogeneous catalyst and is preferably constructed as a distillation or rectification column. The further dehydration of hydroxypropionic acid still present is then carried out in this reactor R2 by heating the fluid F1_1 in the presence of a homogeneous or heterogeneous catalyst to give a fluid F1_2 containing acrylic acid, preferably an aqueous phase P1_2 containing acrylic acid, as the bottom product, this heating being carried out under a pressure $\Pi2$, wherein the pressure $\Pi2$ is generally different from the pressure $\Pi1$ and in a preferred embodiment is lower than $\Pi1$, preferably by at least 0.1 bar, particularly preferably at least 1 bar, moreover preferably at least 2 bar, in addition preferably at least 4 bar, furthermore preferably at least 8 bar and moreover preferably at least 10 bar lower than $\Pi1$. In one embodiment of the process according to the invention, the pressure of the first reactor R1 is in a range of from 4.5 to 25 bar, preferably in a range of from 5 to 20 bar and moreover preferably in a range of from 6 to 10 bar and the pressure of the further reactor R2 is in a range of from 1 to <4.5 bar and preferably in a range of from 2 to 4 bar. In one embodiment of the process according to the invention, the pressure of the first reactor R1 is in a range of from 4.5 to 25 bar, preferably in a range of from 5 to 20 bar and moreover preferably in a range of from 6 to 10 bar and the pressure of the further reactor R2 is in a range of from 0.01 to <1 bar and preferably in a range of from 0.1 to 0.8 bar. Water is separated off as the distillate in this reaction vessel R2. In the reactive distillation, water often leaves overhead in an amount of 20 wt. % and more, preferably 40 wt. % and more and particularly preferably 60 wt. % and more. The remaining water remains in the bottom product of the reactive distillation. The above wt. % are in each case based on 100 wt. % of the component introduced into the reactive column.

In this connection, it is furthermore preferable for both the reactor R1 and the reactor R2 to be gassed with $CO_2$ before the introduction of the fluid F1, of the aqueous phase P1, of the fluid F1_1 or of the aqueous phase P1_1, in order to avoid decarboxylation reactions during the dehydration reaction, as described above.

The catalysts in the reactors R1 and R2 can be identical or different, it being possible for the level of the conversion and the selectivity in the individual reaction vessels to be adjusted via the dwell time in the particular catalyst bed, via the pressure, via the temperature and, in the case of the second reaction vessel, via the reflux ratio. If a homogeneous and usually liquid catalyst, in particular an inorganic acid, such as phosphoric acid, is employed, it is preferable for at least the main amount of this catalyst to be added to the reactor R1.

The dehydration in the reactor R1, which is preferably a closed, pressure-resistant reactor, is, depending on the nature and amount of the catalyst used and depending on the pressure prevailing in the reaction vessel, preferably in a range of from 80 to 200° C., particularly preferably in a range of from 120 to 160° C., while the pressure is preferably in a range of from 1 to 10 bar, particularly preferably from 3 to 8 bar (abs.).

The fluid F1_1 obtained in this reactor R1 or the aqueous phase P1_1 is then introduced into the reactor R2, which is constructed as a distillation or rectification column. In this context, the fluid F1_1 or the aqueous phase P1_1 can be introduced either into the top region of the distillation column, preferably into a region of the upper third, particularly preferably in a region of the upper quarter and most preferably in a region of the upper quarter of the distillation or rectification column, or also in a side region of the distillation or rectification column, preferably in a region between the lower and the upper third, particularly preferably between the lower and the upper quarter of the distillation or rectification column.

If the fluid F1_1 or the aqueous phase P1_1 is introduced into the top region of the distillation or rectification column, in this case the water is preferably distilled off in countercurrent. If the fluid F1_1 or the aqueous phase P1_1 is introduced in the side region of the distillation or rectification column, it is preferable for the distillation or rectification column to include a lower reaction region, in which the catalyst is located, and, adjacent to this reaction region, an upper distillation region which is free from catalyst, and for the fluid F1_1 or the aqueous phase P1_1 to be introduced into the distillation column between the reaction region and the distillation region.

The temperature in the reactor R2 is preferably in the same range as the temperature in the reactor R1, while the pressure is lower, in order to render distillation of the water possible. The pressure of the reactor R2 is preferably lowered by 1 to 5 bar compared with the first reactor R1.

Preferably, an aqueous acrylic acid solution which contains no catalyst constituents (such a solution is obtained in the case of a heterogeneously catalysed dehydration), or an aqueous acrylic acid solution which contains catalysts (such a solution is obtained in the case of a homogeneously catalysed dehydration), as an aqueous phase P2, is obtained as the reaction mixture or as the fluid F2 which is obtained after the dehydration. If the organic phase obtained in a multiple phase separation has been employed as the fluid F1, an organic phase containing acrylic acid, as the fluid F2, is preferably obtained as the reaction mixture which is obtained after the dehydration, this organic phase optionally still containing catalyst constituents, depending on whether a homogeneous or heterogeneous catalyst has been employed.

If an aqueous fermentation solution which optionally has been freed from solids and has optionally been reduced in its water content beforehand, has been employed as the fluid F1, it is preferable for the fluid F2 obtained in process steps (a2) to be an aqueous phase P2 which has a composition C3 comprising:

(C3_1) 20 to 95 wt. %, preferably 30 to 90 wt. % and most preferably 50 to 85 wt. % of acrylic acid, salts thereof or mixtures thereof, (C3_2) 0 to 5 wt. %, preferably 0.1 to 2.5 wt. % and most preferably 0.5 to 1 wt. % of inorganic salts, (C3_3) 0.1 to 30 wt. %, preferably 0.5 to 20 wt. % and most preferably 1 to 10 wt. % of organic compounds which differ from acrylic acid, in particular hydroxypropionic acids, (C3_4) 0 to 50 wt. %, preferably 1 to 40 wt. %, preferably 5 to 20 wt. % and most preferably 1 to 10 wt. % of cells, and (C3_5) 1 to 90 wt. %, preferably 50 to 80 wt. % and most preferably 10 to 70 wt. % of water, wherein the sum of components (C3_1) to (C3_5) is 100 wt. %. Especially if the dehydration of the hydroxypropionic acid has been carried out by means of the reactive distillation process described above, it is preferable for the composition C3 which contains acrylic acid and is obtained as the bottom product in the reactive distillation to contain less than 25 wt. %, particularly preferably less than 10 wt. % and most preferably less than 5 wt. % of water, in each case based on the total weight of the composition C3.

It may furthermore be advantageous to purify the fluid F1 or the fluid F2 by an adsorption process, in particular by purification with a commercially available filter, in particular an active charcoal filter, before process step (a2) or (a3) is carried out.

If no solids, such as, for example, cells, have as yet been separated off, it may be helpful to separate off these solids by the filtration processes described above, for example by ultrafiltration, before carrying out the crystallization in process step (a3).

In process step (a3) of the process according to the invention, the acrylic acid contained in the fluid F2 is now purified by crystallization, preferably by a suspension crystallization or a layer crystallization, to give a purified phase, a suspension crystallization carried out continuously being particularly preferred. In one embodiment of the process according to the invention, the crystallization can already be carried out with the water-rich aqueous phase P2 (or phase F1_1) containing acrylic acid and hydroxypropionic acid, such as is obtained after the dehydration in the first reactor R1. In another embodiment of the process according to the invention, the crystallization is carried out with the phase F1_2 which originates from the further reactor and has a lower water content compared with the phase P2. The phase P2 often contains more than 30 wt. %, preferably more than 50 wt. % and particularly preferably more than 70 wt. % of water in addition to acrylic acid and hydroxypropionic acid. On the other hand, the phase F1_2 often contains less than 30 wt. %, preferably less than 20 wt. % and particularly preferably less than 10 wt. %, in addition to acrylic acid and hydroxypropionic acid.

In the case of suspension crystallization, the crystals can be separated off from the mother liquor by a washing column. For successful operation of a washing column, it is advantageous if the crystals to be washed have a sufficient hardness and have a particular narrow size distribution, in order to ensure a corresponding porosity and stability of the packed or non-packed filter bed formed.

The suspension crystallization can advantageously be realized in a stirred tank crystallizer, scraped surface crystallizer, cooling disk crystallizer, crystallizing screw, drum crystallizer, tube bundle crystallizer or the like. In particular, the crystallization variants mentioned in WO-A-99/14181 can be used for the purpose mentioned. Those crystallizers which can be operated continuously in particular are in turn of particular advantage here. These are preferably the cooling disk crystallizers or the scraped surface cooler (dissertation by Poschmann, p. 14). A scraped surface cooler is very particularly preferably employed for the crystallization.

In principle, any washing column which allows the continuous procedure of the purification according to the invention can be employed for the process according to the invention. In a conventional embodiment, the suspension is introduced into a hydraulic washing column in the upper part of the column. The mother liquor is removed from the washing column via a filter, a densely packed crystal bed forming. The mother liquor flows through the crystal bed in the direction of the base of the column and forces this downwards due to the flow resistance. At the base of the column is a moving, preferably rotating scraping device or scraper, which generates a suspension again from the densely packed crystal bed and the wash melt introduced at the lower part of the washing column. This suspension is preferably pumped off through a melting unit, preferably a heat exchanger, and melted. A part of the melt can serve e.g. as the washing melt; this is then pumped back into the column and preferably washes out the crystal bed migrating in the opposite direction, i.e. the crystallized acrylic acid is washed in countercurrent by the recycled acrylic acid. Against the background of increasing the yield, recycling of the mother liquor which has been separated off is particularly advantageous. The washing melt on the one hand effects washing of the crystals, and on the other hand the melt at least partly crystallizes out on the crystals. The crystallization enthalpy liberated heats the crystal bed in the wash region of the column. A purification effect analogous to sweating of the crystals is thereby achieved.

A purification is therefore effected on the one hand by the washing of the surface of the acrylic acid with molten—and therefore already purified acrylic acid, and on the other hand healing or exudation of impurities is achieved by the crystallization of the molten purified acrylic acid on the acrylic acid crystals already present. This allows a particularly highly pure preparation of acrylic acid.

However, the washing of the crystals obtained by suspension crystallization can in principle also be carried out in a manner other than countercurrent washing in a washing column. Thus, for example, the crystals can be washed on a belt filter after they have been separated off from the mother liquor by means of a suitable separating device, for example a filter.

According to a further embodiment of the process, the aqueous phase P2, preferably the phase F1_2, is cooled to a maximum to the temperature T of the triple eutectic point of a composition of acrylic acid, water and hydroxypropionic acid, preferably down to a temperature which is at most 6 Kelvin, particularly preferably at most 3 Kelvin and most preferably at most 1 Kelvin above the temperature of the triple eutectic point.

Preferably, in the purification by means of crystallization a first crystal phase is obtained, containing:
  at least 30 wt. % of acrylic acid, preferably at least 40 wt. % and most preferably at least 50 wt. % of acrylic acid,
  at least 30 wt. %, preferably at least 40 wt. % and most preferably at least 49 wt. % of water, and
  at most 10 wt. %, preferably at most 5 wt. % and most preferably at most 1 wt. % of hydroxypropionic acid.

The purification of the acrylic acid from the fluid F2, in particular from the aqueous phase P2, by means of crystallization can be carried out in one, two, three or more stages. In a two-stage crystallization, the crystals obtained in the first crystallization stage are separated off from the mother liquor which remains, melted and crystallized again in a second crystallization stage.

Especially if a composition C3 which, in addition to acrylic acid, organic compounds which differ from acrylic acid, such as, in particular hydroxypropionic acid which has not been dehydrated in process step (a2), and optionally inorganic salts, contains more than 5 wt. %, particularly preferably more than 10 wt. % and most preferably more than 25 wt. % of water is employed as the fluid F2, preferably as the aqueous phase P2, according to a particular embodiment of the process according to the invention it is preferable for the crystallization in process step (a3) to be configured as an at least two-stage and preferably at least three-stage crystallization. In the case of the at least two-stage crystallization, it is preferable if in at least two preferably successive stages the particular eutectic of the main components of such a stage, which as a rule are contained in the particular feed with 1 and more wt. %, is approached by varying the crystallization conditions, preferably lowering the temperature. If crystallization is carried out in three and more stages, it is preferably if before the stage in which the eutectic of the particular main components of the feed, preferably water and acrylic acid, is not reached by varying the crystallization conditions, preferably lowering the temperature, at least one, preferably at least two stages in which the particular eutectic of the main components is approached by varying the crystallization conditions, preferably lowering the temperature, are carried out. In the above stages it is preferable for a cooling rate in a range of from 0.01 to 10 K/min, preferably in a range of from 0.05 K/min to 5 K/min and particularly preferably in a range of from 0.1 to 1 K/min to be used.

It is thus furthermore preferable for process step (a3) to comprise the following part steps, which preferably follow one another directly:

(a3_1) crystallization, preferably suspension or layer crystallization, most preferably suspension crystallization, of the fluid F2, in particular of the aqueous phase P2, in a first crystallization stage to give a crystal phase K1 and a mother liquor M1, wherein the crystal phase K1 comprises:
  5 to 60 wt. %, particularly preferably 10 to 55 wt. % and most preferably 15 to 50 wt. % of acrylic acid,
  39.9 to 95 wt. %, particularly preferably 44.6 to 90 wt. % and most preferably 80 to 99.5 wt. % of water, and
  0.1 to 10 wt. %, particularly preferably 0.4 to 8 wt. % and most preferably 1 to 6 wt. % of by-products which differ from water and acrylic acid,
  and wherein the sum of the amounts by weight of acrylic acid, water and by-products is 100 wt. %, (a3_2) separating off of the crystal phase K1 from the mother liquor M1, preferably by means of a washing column, the crystals preferably being subjected to a crystal washing in the nature and manner described above, (a3_3) melting of the crystal phase K1 from the first crystallization stage, (a3_4) renewed crystallization, preferably suspension or layer crystallization, most preferably suspension crystallization, of the molten crystal phase in a second crystallization stage to give a crystal phase CR2 and a mother liquor M2, wherein the crystal phase K2 comprises:
  8 to 35 wt. %, particularly preferably 1 to 28 wt. % and most preferably 0.4 to 19.75 wt. % of acrylic acid,
  at least 60 wt. %, particularly preferably at least 70 wt. % and most preferably 80 to 99.5 wt. % of water, and
  a maximum of 5 wt. %, particularly preferably a maximum of 2 wt. % and most preferably 0.1 to 0.25 wt. % of by-products which differ from water and acrylic acid,
  wherein the sum of the amounts by weight of acrylic acid, water and by-products is 100 wt. %, (a3_5) separating off of the crystal phase K2 from the mother liquor M2, preferably by means of a washing column, (a3_6) crystallization, preferably suspension or layer crystallization, most preferably suspension crystallization, of the mother liquor M2 in a third crystallization stage to give a crystal phase K3 and a mother liquor M3, wherein the crystal phase K3 comprises:
  at least 40 wt. %, particularly preferably at least 50 wt. % and most preferably 55 to 70 wt. % of acrylic acid,
  a maximum of 70 wt. %, particularly preferably a maximum of 57.5 wt. % and most preferably 45 to 57.5 wt. % of water, and
  a maximum of 5 wt. %, particularly preferably a maximum of 2.5 wt. % and most preferably 0 to 1.5 wt. % of by-products which differ from water and acrylic acid,
  wherein the sum of the amounts by weight of acrylic acid, water and by-products is 100 wt. %, and (a3_7) separating off of the crystal phase K3 from the mother liquor M3, preferably by means of a washing column, the crystals preferably being subjected to a crystal washing in the nature and manner described above, a purified phase containing acrylic acid crystals finally being obtained.

In the particular embodiment of the process according to the invention described above with a three-stage crystallization stage in process step (a3), it may be particularly advantageous to feed the mother liquor obtained in the first crystallization stage, which still contains relatively large amounts of non-dehydrated hydroxypropionic acid, back into process step (a2) for the purpose of a dehydration which is as complete as possible.

Embodiments of suspension crystallization with subsequent washing of the crystals in a hydraulic or mechanical washing column are to be found in the book "Melt crystallization technology" by G. F. Arkenbout, Technomic Publishing Co. Inc., Lancaster-Basle (1995), p. 265 to 288 and the article directed at the Niro freeze concentration for preconcentration of waste water in Chemie-Ingenieurtechnik (72) (1Q/2000), 1231 to 1233.

A washing liquid familiar to the person skilled in the art can be used as the washing liquid, depending on the intended use (for aqueous solutions e.g. water). As already indicated, a part amount of the molten crystals of the crystallized acrylic acid, the crystallized water or the crystallized mixture of water and acrylic acid very particularly preferably serves for washing thereof. This measure on the one hand ensures that no further substance has to be introduced into the system for the production of highly pure products, and on the other hand the molten crystals also serve to push back the mother liquor front in the washing column and at the same time have a purifying effect on the crystals, analogously to sweating. In this context, no loss of product takes place since the washing liquid crystallizes out in turn on the crystals to be washed and is recovered in the product in this way (e.g. brochure of Niro Process Technology B.V. Crystallization and wash column separations set new standards in purity of chemical compounds).

In an alternative embodiment, the formation of the crystals in at least one of process steps (a3_1), (a3_4) and (a3_6) is carried out in a layer. A layer crystallization is carried out in accordance with the process of Sulzer AG, Switzerland (http://www.sulzerchemtech.com). A suitable layer crystallizer and the procedure during layer crystallization is described, for example, in WO-A-00/45928, which is introduced herewith as reference and the disclosure content of which with respect to layer crystallization forms a part of the disclosure of the present invention.

In the end, an acrylic acid having a purity of at least 50 wt. %, in particular at least 70 wt. %, preferably at least 90 wt. % can be prepared by the process according to the invention for the preparation of acrylic acid.

The process according to the invention for the preparation of polyacrylates envisages polymerization, preferably free radical polymerization, of an acrylic acid obtainable from the process according to the invention.

The free radical polymerization of the acrylic acid is carried out by the polymerization process known to the person skilled in the art. If the polymers are crosslinked, partly neutralized polyacrylates, reference is made to the 3rd chapter (page 69 et seq.) in "Modern Superabsorbent Polymer Technology", F. L. Buchholz and A. T. Graham (editors), Wiley-VCH, New York, 1998 with respect to the precise procedure.

A contribution towards achieving the abovementioned objects is furthermore made by the acrylic acid obtainable by the process according to the invention for the preparation of acrylic acid, and the polyacrylates obtainable by the process according to the invention for the preparation of polyacrylates.

A further contribution towards achieving the abovementioned objects is made by chemical products containing the polyacrylates according to the invention. Preferred chemical products are, in particular, foams, shaped articles, fibers, foils, films, cables, sealing materials, liquid-absorbing hygiene articles, in particular diapers and sanitary napkins, carriers for plant or fungal growth-regulating agents or plant protection active compounds, additives for building materials, packaging materials or soil additives.

The use of the polyacrylates according to the invention in chemical products, preferably in the abovementioned chemical products, in particular in hygiene articles, such as diapers or sanitary napkins, and the use of the superabsorber particles as carriers for plant or fungal growth-regulating agents or plant protection active compounds also make a contribution towards achieving the abovementioned objects. For the use as a carrier for plant or fungal growth-regulating agents or plant protection active compounds it is preferable for it to be possible for the plant or fungal growth-regulating agents or plant protection active compounds to be released over a period of time controlled by the carrier.

The device according to the invention for the preparation of acrylic acid comprises the following units connected to one another by fluid-carrying lines:
a synthesizing unit for the preparation of hydroxypropionic acid from a biological material to give a fluid F1 containing hydroxypropionic acid, in particular an aqueous phase P1,
a dehydration stage for the hydroxypropionic acid to give a fluid F2 containing acrylic acid, in particular an aqueous phase P2, and
a purification unit for the fluid F2 containing acrylic acid by a suspension crystallization or a layer crystallization to give a purified phase.

According to the invention, "by fluid-carrying lines" is understood as meaning that gases or liquids, suspension included, or mixtures thereof are led through corresponding lines. Pipelines, pumps or the like can be employed in particular for this.

Hydroxypropionic acid is synthesized from a regenerable raw material with the aid of the synthesizing unit, and is subsequently converted into acrylic acid by means of the dehydration stage. The acrylic acid is then purified in the context of a layer crystallization or a suspension crystallization. In addition to a conventional bioreactor, the device according to the invention can also include a sterilization unit, in which the microorganisms contained in the fermentation broth can be killed after the fermentation has ended, a filtration unit, in which solids contained in the fermentation broth can be separated off by filtration, preferably by ultrafiltration, a protonation unit, in which at least a part of the hydroxypropionic acid optionally present as a salt can be converted into its acid form, and/or a dewatering unit, in which at least a part of the water can be separated off. In this context, these units can be located both between the synthesizing unit and the dehydration stage and between the dehydration stage and the purification unit, at least the sterilization unit and the filtration unit preferably being located between the synthesizing unit and the dehydration stage.

According to a preferred embodiment of the device according to the invention, the dehydration stage is constructed as a pressure reactor, it furthermore being particularly preferable for the dehydration stage to include a distillation or rectification device which contains one of the dehydration catalysts described above. The reactive distillation described in connection with the process according to the invention for the preparation of acrylic acid can be carried out by means of such a dehydration stage. All the known forms of construction of distillation columns, in particular packed columns and plate columns, are suitable as the device for this purpose.

In this context it may be particularly advantageous if the dehydration stage has at least two dehydration reactors R1 and R2 which are connected to one another by fluid-carrying lines and which all contain one of the dehydration catalysts described above, one of which can be loaded with a pressure $\Pi 1$ and the other with a pressure $\Pi 2$, where the two pressures differ from one and the pressure $\Pi 2$ is preferably lower than $\Pi 1$. The preferred pressure differences are those pressure differences which have already been described above in connection with the process according to the invention. Preferably, the reactor R2 is constructed as a distillation or rectification device and the reactor R1 is not. This distillation or rectification device is connected to the purification unit such that the bottom product obtained in the distillation or rectification can be transferred into the purification unit.

At least a part of the hydroxypropionic acid is converted into acrylic acid by means of the dehydration reactor R1, into which the fermentation solution which has preferably been freed from solids and optionally at least partly dewatered is introduced. In this context, the first dehydration reactor R1 is preferably connected to the second dehydration reactor R2 such that the aqueous solution which contains hydroxypropionic acid, acrylic acid and water and is obtained in the first reactor R1 is introduced into the top region of the second reactor, preferably into a region of the upper third, particularly preferably in a region of the upper quarter and most preferably in a region of the upper quarter of the reactor R2, or also in a side region of the reactor R2, preferably in a region between the lower and the upper third, particularly preferably between the lower and the upper quarter of the reactor R2. The circumstance that for a reactive distillation the low liquid content of the packed columns employed for the rectification is a disadvantage, especially in the case of reactions with a finite rate of reaction, can be taken into account by means of the reactor R1. In order to achieve the desired conversions in slow reactions, a long dwell time of the liquid in the apparatus must be ensured. As an aid, in addition to the column one or more external tanks (reactor 1, further external tanks (reactors, R1', R1" etc.) can optionally also be present) in which a major part of the actual reaction takes place can be installed. Recycling of the liquid from these tanks into the column in each case requires division of the packing and an elaborate distribution of liquid, so that plate columns with comparatively high liquid contents are advantageously employed for the reactive distillation. Plate columns have a high liquid content, and indeed both in the two-phase layer on the plate and in the downcomers. Both portions of the liquid content can be modified in a targeted manner and adapted to the reactive distillation by construction measures, i.e. by the design of the plates or the height of the weirs. The following aspects play an important role when designing suitable built-in components for a reactive plate column: (i) realization of very high liquid contents, i.e. dwell times; (ii) distribution of the hold-up over the column height as desired; (iii) suitability both for homogeneous and for heterogeneous catalysis; (iv)

easy replacement of the catalyst; (v) simple scale-up from the laboratory to large-scale industrial columns.

The fluid F2 containing the acrylic acid can be purified by a suspension crystallization or a layer crystallization by means of the purification unit to give a purified phase.

According to a particularly preferred embodiment of the device according to the invention, the purification unit includes the following constituents connected to one another by fluid-carrying lines:

(δ1) a first crystallization region, a second crystallization region, a third crystallization region, a first separating region, a second separating region, a third separating region, at least one melting unit and at least six guide lines, (δ2) the first crystallization region is connected to the first separating region via a first guide line, (δ3) the first separating region is connected to the at least one melting unit via a second guide line, (δ4) the at least one melting unit is connected to the second crystallization region via a third guide line, (δ5) the second crystallization region is connected to the second separating region via a fourth guide line, (δ6) the second separating region is connected to the third crystallization region via a fifth guide line, (δ7) the third crystallization region is connected to the third separating region via a sixth guide line.

In this context it is preferable for the dehydration stage preferably to be connected directly to the first crystallization region by fluid-carrying lines, in the case of a reactive distillation or rectification column in the dehydration stage these columns preferably being connected to the first crystallization unit such that the bottom product obtained can be transferred into the crystallization unit. In one embodiment according to the invention, this crystallization device according to the invention having several successive crystallization regions can follow the first reactor R1. Very pure aqueous acrylic acid solutions can be obtained in this way, so that a polymerization device in which this acrylic acid solution is polymerized can follow the crystallization device directly.

If suspension crystallizers are employed as crystallization regions and washing columns are employed as separating regions, with this particular embodiment of the device according to the invention the fluid F2 which contains acrylic acid and is obtained in the dehydration stage can be crystallized in the first crystallization region to give crystals of water and acrylic acid. These can then be washed in a washing column (first separating unit) and separated off from the mother liquor which remains and which above all still contains hydroxypropionic acid. The crystals separated off, which above all contain water and acrylic acid, can then be melted in the at least one melting unit and then crystallized again in the second crystallization region. The crystals which are obtained in this second crystallization region and above all are based on water can be separated off from the mother liquor in a further washing column (second separating unit). The mother liquor which remains can then be crystallized in a third crystallization region to give crystals which are essentially based on acrylic acid, it being possible for these crystals then to be washed in a further washing column (third separating unit) and separated off from the mother liquor which remains.

According to an embodiment, which is furthermore advantageous, of the particularly preferred embodiment described above for the device according to the invention in which three crystallization regions are present, the first separating unit and the third separating unit are connected to a second and, respectively, a third melting unit by fluid-carrying lines. The crystals which have been separated off from the mother liquor in the first and third separating unit can be at least partly melted with this second and, respectively, third melting unit, and the crystal melts obtained in this way can be employed for the countercurrent washing of the crystal phases present in the particular separating units, as is described, for example, in DE-A-101 49 353.

Because of the purification method, the acrylic acid prepared in this way is treated particularly gently, as a result of which its quality is improved. The purification device is capable of obtaining very pure acrylic acid having purities of more than 60 percent by weight, in particular of more than 99.5 percent by weight, from a comparatively contaminated acrylic acid stream, which above all contains water and hydroxypropionic acid as by-products, of about 12 percent by weight. According to the invention, it is possible to purify efficiently an acrylic acid stream with 50 percent by weight to 95 percent by weight of acrylic acid, preferably 75 to 90 percent by weight of acrylic acid.

The effective purification enables further thermal treatment methods, in particular a distillation or evaporation, to be reduced, so that exposure of the acrylic acid and the acrylic acid formed therefrom to heat is reduced. As a result, the quality of the acrylic acid and of the acrylic acid is improved.

To further increase the purity of the acrylic acid, the device unit has a separate purification device. This separate purification device can be employed for further purification of the end product, in particular for further purification of the acrylic acid leaving the melting unit.

To increase the yield, it is particularly preferable for the first separating region to be connected to the dehydration reactor, so that the mother liquor obtained in the separating region can be introduced into the dehydration stage again for the purpose of a conversion of the hydroxypropionic acid which is as complete as possible.

In the process according to the invention for the purification of acrylic acid, temperatures in the range of from −20 to +20° C., preferably from −10 to +13° C. under a pressure of from 1 to 10 bar prevail in the separating regions. It is preferable for a lower temperature and a lower pressure to prevail in the lower region of the separating regions than in the upper region of the separating regions. Preferably, −20 to <12° C. under a pressure of 1 to 2 bar prevail in the lower region of the separating regions. In the upper region of the separating regions, a temperature of at least 12° C. and a pressure of from 1 to 10 bar, preferably 3 to 7 bar prevail. Advantageously, temperatures in the range of from −20 to 20° C., preferably from −12 to 13° C. under a pressure of from 0.5 to 10 bar, preferably from 0.8 to 2 bar prevail in the crystallization regions. A temperature in the range of from 10 to 50° C., preferably from 11 to 10° C. under a pressure of from 1 to 10 bar, preferably 3 to 7 bar can prevail in the at least one melting unit.

In the guide lines, temperature and pressure conditions which allow a reliable and trouble-free transportation of the acrylic acid and the substances which optionally accompany this in these guide lines prevail.

The device allows a relatively contaminated acrylic acid, which optionally still contains large amounts of water and hydroxypropionic acid, to be used as the starting material, as a result of which the preliminary outlay for a distillation of the acrylic acid originating from the synthesis becomes lower. In particular, the exposure of the acrylic acid to heat, which can lead to undesirable polymerization, or to a premature formation of acrylic acid, undesirable polymerization resulting therefrom, is therefore lowered.

In a modification of the invention, in particular in combination with the device according to the invention for the preparation of acrylic acid by means of a layer crystallization or a suspension crystallization, a device according to the invention for the preparation of acrylic acid comprises the following units connected to one another by fluid-carrying lines:

a synthesizing unit for 3-hydroxypropionic acid from a biological material to give a fluid, in particular aqueous, phase containing 3-hydroxypropionic acid, a dehydration stage for the 3-hydroxypropionic acid to give a fluid, in particular aqueous, solution containing acrylic acid and at least one of the following separating devices (S1) to (S5) as a dewatering unit:
(S1) reverse osmosis device,
(S2) electroosmosis device,
(S3) azeotropic distillation device,
(S4) electrodialysis device,
(S5) multiple phase separation device.

This modification can be employed in particular as a preliminary stage before the purification unit. It is also preferable in particular for at least one of the separating devices (S1) to (S5) to be inserted between process steps (a1) and (a3), in particular between (a1) and (a2), in order to achieve a pre-purification effect.

The reverse osmosis device is suitable for carrying out a reverse osmosis; the electroosmosis device is suitable for carrying out an electroosmosis, the azeotropic distillation device is suitable for carrying out an azeotropic distillation; the electrodialysis device is suitable for carrying out an electrodialysis; the multiple phase separation device is suitable for carrying out a multiple phase separation, in particular the abovementioned "salt splitting".

In a specific further development, the device comprises a further separating device, in particular filter, for separating off solids, in particular particles, such as microorganisms, cells or parts thereof, from the fluid phase, from the fluid solution or from both. The further separating device for separating off solids is preferably located, as already described above, between the synthesizing unit and the dehydration stage. The separate separating device for separating off solids can also be arranged between the dehydration stage and the purification unit or the separating devices (S1) to (S5).

The device furthermore advantageously comprises a protonation means for the hydroxypropionic acid in the fluid phase. The protonation can be carried out in particular by addition of an acid, for example hydrochloric acid, or ammonium chloride. The protonation means can also be an ion exchanger, with which the hydroxypropionic acid is converted into the free acid.

The protonation means is arranged in particular downstream of the synthesizing unit, i.e. in particular between the synthesizing stage and the dehydration stage or between the dehydration stage and one of the separating devices (S1) to (S5) functioning as a dewatering unit or the purification unit. The protonation means can also be arranged directly at the dehydration stage or purification unit or separating device (S1) to (S5) and can be a feed for a reagent which effects protonation of the hydroxypropionic acid, such as e.g. an acid.

The device can have adsorption means or absorption means, in particular an active charcoal filter, for further purification of the fluid phase or of the fluid solution, or both. Fine particles in the suspension, such as e.g. biological residues, can be removed from the fluid phase or solutions with the aid of the ad- or absorption means, it being possible for this absorption means to be located both between the synthesizing unit and the dehydration stage and between the dehydration stage and the purification unit.

The device according to the invention for the preparation of polyacrylates comprises the device according to the invention for the preparation of acrylic acid and a polymerization reactor for the polymerization of acrylic acid, in particular a polymerization reactor for the free radical polymerization of acrylic acid.

In a preferred embodiment of the process according to the invention for the preparation of acrylic acid, the device described above is employed.

In the process according to the invention for the preparation of polyacrylates, an acrylic acid obtained by the process according to the invention is polymerized, this polymerization preferably being carried out in the presence of crosslinking agents. If the polymers are crosslinked, partly neutralized polyacrylates (so-called superabsorbers), reference is made to the 3rd chapter (page 69 et seq.) in "Modern Superabsorbent Polymer Technology", F. L. Buchholz and A. T. Graham (editors), Wiley-VCH, New York, 1998 with respect to the precise procedure.

The polyacrylates according to the invention are preferably characterized by a sustainability factor of at least 10, preferably at least 20, particularly preferably at least 50, moreover preferably at least 75, in addition preferably at least 85 and furthermore preferably at least 95. In this context, the sustainability factor indicates the proportion to which the water-absorbing polymer structure is based on non-fossil regenerating organic material. If the sustainability factor is 100, the polymer structure comprises entirely substances based on non-fossil regenerating organic materials.

The polyacrylates obtained by the process according to the invention for the preparation of polyacrylates are preferably a water-absorbing polymer structure. This water-absorbing polymer structure preferably has at least one of the following properties:

($\beta$1) a CRC value (CRC=centrifugation retention capacity), determined in accordance with ERT 441.2-02 (ERT=edana recommended test method), of at least 20 g/g, preferably at least 25 g/g and most preferably at least 30 g/g, a CRC value of 60 g/g, preferably of 50 g/g not being exceeded;

($\beta$2) an absorption against a pressure of 0.7 psi (AAP), determined in accordance with ERT 442.2-02, of at least 16 g/g, preferably at least 18 g/g and most preferably at least 20 g/g, a value of 50 g/g, preferably of 40 g/g not being exceeded.

The fibers, films, molding compositions, textile and leather auxiliaries, flocculating agents, coatings or lacquers according to the invention are based on acrylic acid which has been obtained by the process according to the invention or on derivatives thereof, such as, for example, on esters of this acrylic acid, while according to the use according to the invention of the acrylic acid obtained by the process according to the invention for the preparation of acrylic acid, this or its derivatives is or are preferably employed in fibers, films, molding compositions, textile and leather auxiliaries, flocculating agents, coatings or lacquers.

Advantageous details and embodiments, which can in each case be used, or combined with one another as desired, are explained further with the aid of the following drawings, which are not intended to limit the invention but merely to illustrate it by way of example.

FIG. 1 illustrates the process flow according to the invention and the device according to the invention. Via the feed 1 for biomass, such as e.g. rape or maize, this can be introduced into the synthesizing unit 2, the synthesizing unit 2 preferably being a bioreactor. In the synthesizing unit 2 the biomass is converted to form an aqueous phase P1 containing hydroxypropionic acids, preferably 2- or 3-hydroxypropionic acids, most preferably 3-hydroxypropionic acid. This aqueous phase P1 can then be fed via an outlet 3 to a killing unit, which is, for example, an autoclave or another sterilization device known to the person skilled in the art. The aqueous phase P1 treated in this way can then be fed via the outlet 5 to a filtration unit 6, in which the aqueous phase P1 is freed from solids, such as, for example, microorganisms. The solids separated off can be removed via a discharge 7. If the microorganisms contained in the aqueous phase P1 are not to be killed and are to be used for a further synthesis cycle, the solids separated off in the filtration unit 6 can also be at least partly fed back into the synthesizing unit (not shown in FIG. 1). (The units 111, 112, 113 and 114 can also be arranged individually or in combination between the synthesizing unit 2 and the dehydration stage 9, not shown in FIG. 1).

The aqueous phase P1 which has been freed from solids then enters, via the outlet 8, into the dehydration stage 9, in which the hydroxypropionic acid is converted into acrylic acid, water being split off. The aqueous phase P2 containing acrylic acid and optionally appropriate unreacted hydroxypropionic acid can then be further treated in further device constituents via the outlet 10. These further device constituents can be, for example, a further filtration unit 111, a protonation means 112, an adsorption means 113 or a dewatering unit 114, for example a reverse osmosis device, an electroosmosis device, an azeotropic distillation device, an electrodialysis device or a multiple phase separation device. These device units can be arranged individually or in combination in series between the dehydration stage 9 and the purification unit 13. It may furthermore be advantageous to arrange one or more of these further device constituents 11 between the synthesizing unit 2 and the dehydration stage 9, particularly preferably between the filtration unit 6 and the dehydration stage 9, instead of or in addition to its arrangement between the dehydration stage 9 and the purification unit 13 (not shown in FIG. 1).

Figure 2:
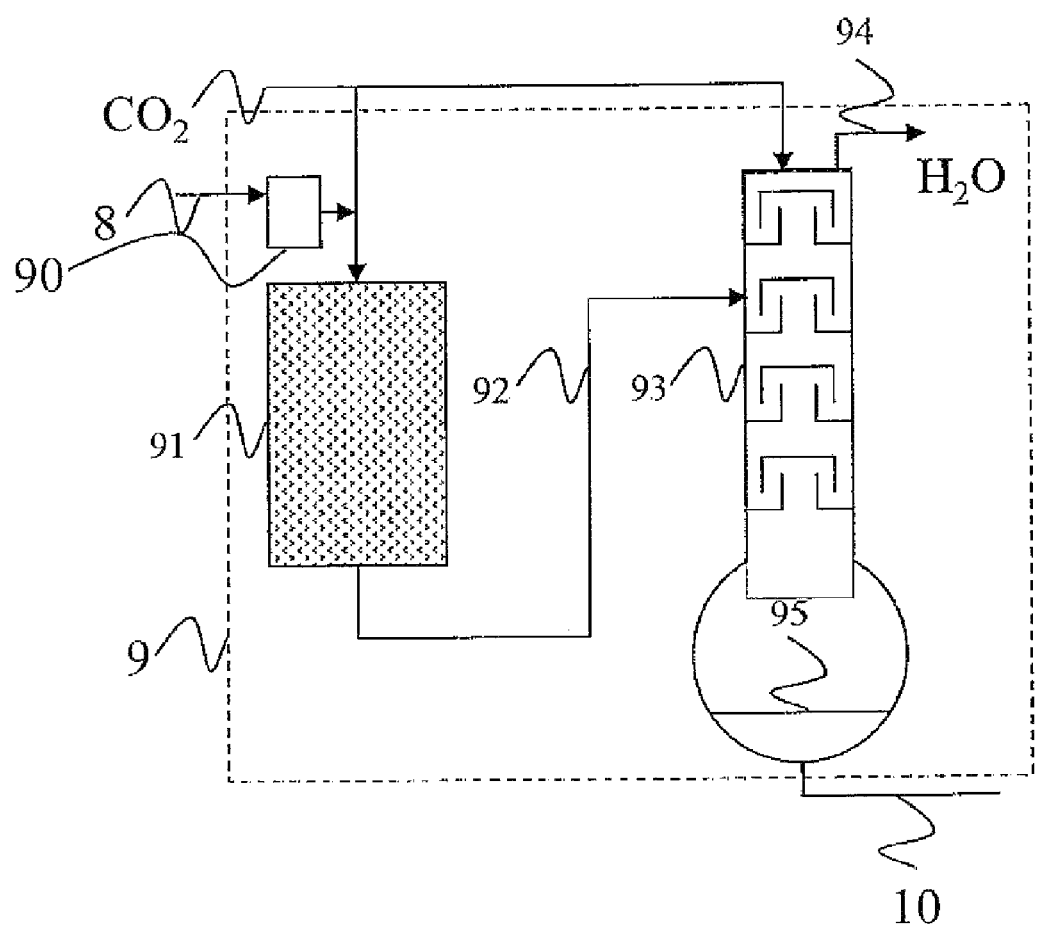
FIG. 2 is a detailed illustration of the dehydration stage shown in FIG. 1 wherein the dehydration stage is being carried out by means of reactive distillation.

FIG. 2 illustrates a preferred embodiment of the process flow according to the invention and of the device according to the invention, in which the dehydration is carried out by means of reactive distillation. Via the outlet 8, via which the aqueous phase P1 which has been freed from solids in the filtration unit 6 is removed, this aqueous phase P1 enters, usually via a membrane 90, into a first reactor 91, which contains a catalyst which promotes the dehydration and in which at least a part of the hydroxypropionic acid is converted into acrylic acid. An aqueous phase P2 containing acrylic acid, water, unreacted hydroxypropionic acid and optionally further by-products is then transferred via a discharge line 92 into a second reactor 93, which is, for example, a distillation or rectification column which likewise contains a catalyst which promotes the dehydration. In this second reactor 93 the hydroxypropionic acid which has not yet reacted is now converted further into acrylic acid, and at the same time the water contained in the aqueous phase is separated off via the discharge 94 (reactive distillation). The bottom product 95 which is obtained in the second reactor 93 and contains the acrylic acid can then be fed via the discharge line 10 to the further device constituents 11 or directly to the purification unit 14 (see FIG. 1). Both the first reactor and the second reactor can be charged with carbon dioxide via a feed line 96, in order to prevent decarboxylation reactions during the dehydration.

Figure 3:
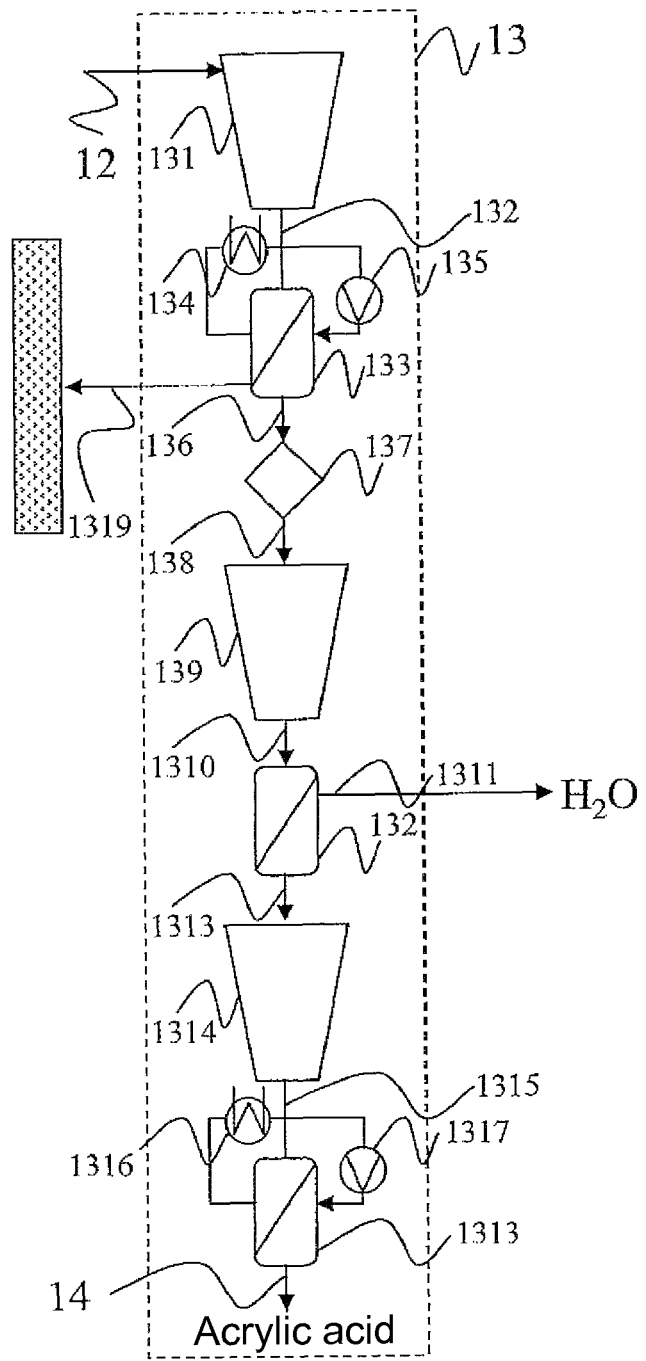
FIG. 3 is a detailed illustration of the purification unit shown in FIG. 1 wherein the purification is being carried out in a three-stage crystallization.

FIG. 3 likewise shows a preferred embodiment of the process flow according to the invention, wherein in this embodiment the purification is carried out in a three-stage crystallization. The aqueous phase P2 treated in the further device constituents 11 or the aqueous phase P2 obtained directly from the dehydration stage 9 enters via the feed 12 into a first crystallization device 131, which is preferably a suspension crystallizer. However, the use of other crystallization devices, such as, for example, a layer crystallizer, is also conceivable. The aqueous phase P2 containing acrylic acid is preferably cooled in the first crystallization device 131 to the extent that water and acrylic acid crystallize out. If a suspension crystallizer is employed as the first crystallization device, the crystal suspension obtained in this way is fed via the discharge line 132 to a first separating region 133, which is preferably a washing column and in which the crystals are separated off from the mother liquor which remains. If a layer crystallizer is employed as the first crystallization device, the use of a separating unit is not essential (not shown in FIG. 3), since in this case it is not necessary to separate off the crystals from the mother liquor, for example by means of a washing column, due to the immobilizing of the crystals on the surfaces of the layer crystallizer. The crystals separated off from the mother liquor in the first separating unit can be at least partly melted by means of a melting unit 134 for the purpose of further increasing the purity, and the molten crystals can be employed, by means of a conveying element 135, for example by means of a pump, for washing the crystals in countercurrent, as is described in DE-A-101 49 353. If a layer crystallizer has been employed as the first crystallization device 131, it may also be advantageous here to at least partly melt the crystals and to employ the crystal melt obtained for washing the crystals in countercurrent.

The crystals which are obtained in the first separating region after the mother liquor has been separated off and essentially comprise water and acrylic acid can then be fed via the discharge line 136 to a melting unit 137, in which the crystals are melted as completely as possible. The mother liquor which remains and which can still contain relatively large amounts of unreacted hydroxypropionic acid can advantageously be fed back via the discharge line 1319 into the dehydration stage 9. The crystals melted in this way are then fed via the discharge line 138 to a second crystallization device 139, in which the temperature is lowered to the extent that crystals essentially comprising water are formed. This second crystallization device is likewise preferably a suspension crystallizer, but the use of a layer crystallizer is also conceivable here. If a suspension crystallizer has been employed as the second crystallization device 139, the crystal suspension obtained in the second crystallization device 139 can then be fed by means of the discharge line 1310 to a second separating region 132, in which the crystals essentially based on water are separated off from the mother liquor essentially based on acrylic acid and water via a discharge 1311. Here also, in the case where a layer crystallizer is employed as the crystallization device, the use of a separate separating unit, such as, for example, a washing column, is not essential.

The mother liquor separated off from the crystals in the second separating region 132 can then be fed via the discharge line 1313 to the third crystallization device 1314, in which the temperature is lowered to the extent that crystals essentially based on acrylic acid are formed. This third crystallization device 1314 can likewise be a suspension crystallizer or a layer crystallizer. If a suspension crystallizer has been employed in the third crystallization device, the crystal suspension obtained in the third crystallization device can be fed via the discharge line 1315 to the third separating region 1316, in which the acrylic acid crystals are separated off from the mother liquor. As is also the case with the first crystallization stage, it may be advantageous to melt at least a part of the crystals in the third separating region by means of a melting unit 1317 and then to employ the melt, via a conveying element 1318, such as, for example, a pump, for washing the crystals in countercurrent. The acrylic acid crystals obtained in the third separating region 1316 can then be removed via a discharge line 14. If a layer crystallizer has been employed as the third crystallization device 1314, it may also be advantageous here to at least partly melt the crystals and to employ the molten crystals for washing the crystals.

The present invention is now explained in more detail with the aid of non-limiting examples.

EXAMPLES

Preparation Example 1

Preparation of a test composition 1 simulating a fermentation broth and comprising:
1,000 ml of water
100 g of 3-hydroxypropionic acid (10 wt. %)
9 g of baker's yeast
1 g of glucose as organic material,
a pH of from 6.5 to 7.5 having been established by means of ammonia.

Preparation Example 2

Preparation of a test composition 2 simulating a purified fermentation broth and comprising:
1,000 ml of water
100 g of 3-hydroxypropionic acid (10 wt. %)

Dehydration 1:

In a device shown in FIG. 2, the solution obtained in Preparation Example 1 is first freed from the yeast by a membrane 90 (commercially obtainable from Amafilter GmbH) and heated in a first pressure reactor 91 (flow-through high-grade steel reactor tube having an internal diameter of 17 mm and a length of 50 cm) at a temperature of 140° C. under a pressure of 8 bar over a dwell time of 8 minutes in the presence of phosphoric acid in a concentration of 1 part of phosphoric acid per 5,000 parts of educt stream.

The reaction mixture obtained in this way, which above all contains water, unreacted 3-hydroxypropionic acid and acrylic acid, was subsequently introduced into a reaction column 93 (autoclave with attached distillation column) and likewise heated at a temperature of 140° C. under a pressure of 3.7 bar over a dwell time of 16 minutes in the presence of the phosphoric acid initially employed, as a catalyst. During this procedure, the water contained in the reaction mixture was separated off over the top and a bottom product rich in acrylic acid was obtained.

Dehydration 2:

Dehydration 1 was repeated here with the following differences: The reaction mixture obtained from the pressure reactor 91, which above all contains water, unreacted 3-hydroxypropionic acid and acrylic acid, was subsequently introduced into a reaction column 93 (autoclave with attached distillation column) and likewise heated at a temperature of 120° C. under a pressure of 500 bar over a dwell time of 45 minutes in the presence of the phosphoric acid initially employed, as a catalyst. During this procedure, the water contained in the reaction mixture was separated off over the top and a bottom product rich in acrylic acid was obtained.

Dehydration 3:

Dehydration 1 was repeated here with the following differences: Instead of phosphoric acid, $CO_2$ was fed into the reactor 91 to saturation.

Dehydration 4:

Dehydration 1 was repeated here, with the difference that test composition 2 was employed.

Dehydration 5:

Dehydration 2 was repeated here, with the difference that test composition 2 was employed.

Dehydration 6:

Dehydration 3 was repeated here, with the difference that test composition 2 was employed.

The bottom products of the above dehydrations have the compositions shown in Table 1.

TABLE 1

|  | Dehydration | | |
|---|---|---|---|
|  | 1 | 2 | 3 |
| Water | 3% | 4% | 4% |
| 3-Hydroxypropionic acid | 11% | 15% | 18% |
| Acrylic acid | 85% | 80% | 77% |
| Glucose | 1% | 1% | 1% |

|  | Dehydration | | |
|---|---|---|---|
|  | 4 | 5 | 6 |
| Water | 6 | 5% | 6% |
| 3-Hydroxypropionic acid | 9% | 15% | 18% |
| Acrylic acid | 87% | 79% | 76% |

Working Up 1

The bottom product of dehydration 1, which was rich in acrylic acid, was fed to a suspension crystallizer (MSMPR "mixed suspension mixed product removal" type as described in Arkenbout G. F. "Melt Crystallization Technology", Lancaster, Technomic Publishing Company Inc. 1995) with a volume of 1 l and was cooled down to an equilibrium temperature of 0° C. with a temperature ramp of 0.25 K/min. The crystal suspension obtained, with a solids content of approx. 50 wt. %, was separated into crystals and contaminated mother liquor via a conventional laboratory suction filter. Thereafter, the crystals were washed with purified acrylic acid (99.5 wt. %) in a weight ratio (crystals/purification liquid) of 5:1 and freed from adhering impurities. The purified crystals were brought to room temperature and thereby melted. An acrylic acid having a purity of 99.5 wt. % was obtained by this procedure. The compositions of the phases (feed, crystals and mother liquor) are given in Table 2.

TABLE 2

|  | Feed | Crystal phase | Mother liquor |
|---|---|---|---|
| Water | 3% | 0.1% | 5.9% |
| 3-Hydroxypropionic acid | 11% | 0.37% | 21.63% |
| Acrylic acid | 85% | 99.5% | 70.5% |
| Glucose | 1% | 0.03% | 1.97% |

Dehydration 7

Dehydration 4 was repeated, with the difference that the dehydration product was let down directly after the pressure reactor 91 and has the composition given in feed 1, Table 3.

Working Up 2

Stage A)

The water-rich acrylic acid mixture of feed 1 was introduced into a 1 l stirred crystallizer and cooled down to a temperature of −18° C., close to the triple eutectic point, with a temperature ramp of 0.25 K/min. The suspension was subsequently filtered over a conventional laboratory suction filter. The crystals obtained were warmed to room temperature and melted. The compositions of the crystals 1 and the mother liquor 1 are listed in Table 1. The crystallization was carried out analogously several times in order to obtain an appropriate amount of product for the following crystallization steps.

Stage B)

The crystal phase 1 of stage A predominantly comprising water and acrylic acid was introduced in turn into a 1 l stirred crystallizer and cooled down to a temperature of −10° C. with a temperature ramp of 0.25 K/min. Crystallization of this virtually binary system of water and acrylic acid was interrupted before the binary eutectic was reached, so that essentially water crystallizes in a targeted manner. Thereafter, the suspension obtained was drained out of the crystallizer and separated into crystals and mother liquor over a laboratory suction filter. The compositions of the mother liquor 2 and the crystal phase 2 are likewise listed in Table 3. This crystallization was likewise carried out several times in order to provide an appropriate amount for use for the following crystallization step.

Stage C)

The mother liquor 2 of stage B with a virtually eutectic composition of water and acrylic acid was introduced into a stirred crystallizer and cooled down to approx. −15° C., below the binary eutectic point, with a temperature ramp of 0.25 K/min. The suspension of crystals of water and acrylic acid formed by this procedure was passed over a laboratory suction filter and filtered. The compositions of the mother liquor 3 and the crystal phase 3 are likewise listed in Table 3.

TABLE 3

| | Stage A) | | |
|---|---|---|---|
| | Feed 1 | Crystal phase 1 | Mother liquor 1 |
| Water | 80.0% | 79.0% | 80.4% |
| 3-Hydroxypropionic acid | 5.0% | 1.0% | 6.7% |
| Acrylic acid | 15.0% | 20.0% | 12.9% |

| | Stage B) | | |
|---|---|---|---|
| | Feed 2 = Crystal phase 1 | Crystal phase 2 | Mother liquor 2 |
| Water | 79.0% | 99.5% | 35.2% |
| 3-Hydroxypropionic acid | 1.0% | 0.02% | 3.1% |
| Acrylic acid | 20.0% | 0.48% | 61.7% |

| | Stage C) | | |
|---|---|---|---|
| | Feed 3 = Mother liquor 2 | Crystal phase 3 | Mother liquor 3 |
| Water | 35.2% | 38.0% | 30.1% |
| 3-Hydroxypropionic acid | 3.1% | 0.00% | 9.6% |
| Acrylic acid | 61.7% | 62.00% | 66.4% |

An acrylic acid/water phase having an acrylic acid content of 62% and a water content of 38% was thereby obtained.

The monomer solution obtained from the crystallization comprising 260 g of acrylic acid (62%), which was neutralized to the extent of 70 mol % with sodium hydroxide solution (202.054 g of 50% strength NaOH), 160 g of water (38%), 0.409 g of polyethylene glycol 300 diacrylate and 1.253 g of monoallyl polyethylene glycol 450 monoacrylate are freed from dissolved oxygen by flushing with nitrogen and cooled to the start temperature of 4° C. When the start temperature was reached, the initiator solution (0.3 g of sodium peroxydisulphate in 10 g of $H_2O$, 0.07 g of 35% strength hydrogen peroxide solution in 10 g of $H_2O$ and 0.015 g of ascorbic acid in 2 g of $H_2O$) was added. When the end temperature of approx. 100° C. was reached, the gel formed was comminuted with a meat chopper and dried in a drying cabinet at 150° C. for 2 hours. The dried polymer was coarsely crushed, ground by means of an SM 100 cutting mill with a 2 mm Conidur perforation and sieved as powder A to a particle size of from 150 to 850 nm.

100 g of powder A are mixed with a solution comprising 1.0 g of ethylene carbonate (EC), 0.6 g of $Al_2(SO_4)_3 \times 14\, H_2O$ and 3 g of deionized water, the solution being applied to the polymer powder in a mixer by means of a syringe with a 0.45 mm cannula. The powder A coated with the aqueous solution was subsequently heated in a circulating air cabinet at 185° C. for 30 minutes. A powder B was obtained (particles sizes: on 150 μm mesh width 13%, on 300 μm mesh width 15%, on 400 μm mesh width 12%, on 500 μm mesh width 15%, on 600 μm mesh width 20%, on 710 to 850 μm mesh width 25%). The properties of this powder are given in Table 4.

TABLE 4

| | Coating with | | Properties | |
|---|---|---|---|---|
| Powder | EC [wt. %] | Al sulphate [wt. %] | CRC [g/g] | $AAP_{(0.7\,psi)}$ [g/g] |
| A | 0 | 0 | 33.8 | 20* |
| B | 1.0 | 0.6 | 29.6 | 23.7 |

*determined at 0.3 psi

Test Methods

Melting Point Determination Via DSC

Apparatus:

DSC 820 from Mettler Toledo with FRS5 ceramic sensor and silver furnace (−150 to 700° C.)

Principle:

The temperature (the temperature range) of the phase transition from the solid into the liquid state is determined. In practice, a sample of the substance to be analysed is heated under atmospheric pressure, the temperatures of the start of melting and of complete melting being determined. Differential scanning calorimetry (DSC) is employed as the method. According to DIN 51 005, this is understood as meaning a thermoanalytical method in which by measuring the temperature difference on a defined heat conduction zone between the sample and reference, which are subjected to the same temperature programme simultaneously, quantitative recording of the difference in heat flow is made possible. This heat flow is measured and plotted as a function of the reference temperature. The proportionality constant K, i.e. the calibration factor, depends on the heat resistance and therefore depends on the temperature. It must be determined by experiment. Melting is associated with an endothermic change in enthalpy, crystallization (freezing, solidification) with an exothermic change.

Melting Point:

That temperature at which the transition between the solid and liquid phase takes place under atmospheric pressure is called the melting temperature. Under ideal conditions this temperature corresponds to the freezing temperature. Since in many substances the phase transition takes place in a temperature range, this transition is also often called the melting range. For pure substance there is only one effective melting point, i.e. only a single temperature at which the solid and liquid are in equilibrium. All impurities and admixtures of other components or e.g. a second or third main component result in a melting range in which the two phases, melt and solid, occur simultaneously with different compositions over a certain temperature range. The start of melting is indicated here with the extrapolated onset temperature. The melting range indicates the effective two-phase region in which the melt and solid are in thermodynamic equilibrium. It is often not sufficient to describe the melting of a substance only with the melting point. Recording of the entire course of melting is indicated above all if the substance is not pure but is a mixture of several similar substances, other substances or modifications (polymorphism), and possibly shows simultaneous decompositions. Plastics with a wide crystallite melting range also require determination of the entire melting behaviour.

Evaluation:

The DSC measurement data are shown on a curve in which the difference in heat flow or the temperature difference assigned to this is plotted against temperature or time. In this context, differences in heat flow from endothermic processes are plotted in the positive ordinate direction, and those from exothermic processes in the negative ordinate direction (see DIN 51007). For characterization of a melting peak, according to DIN 51004 the following temperatures can be used (see FIG. 4): peak onset temperature, extrapolated peak onset temperature, peak maximum temperature, extrapolated peak end temperature and peak end temperature (for terminology see DIN 51005). The extrapolated peak onset temperature is counted as the melting temperature. The peak maximum temperature (with an exponential drop of the peak flank) corresponds to the clear melting point, i.e. the end of the melting range where the molten substance is no longer clouded by suspended crystals. It is also called the melting point of the last crystals or liquidus point.

Definition of Characteristic Temperatures of a Peak (According to DIN 51004)

Figure 4:
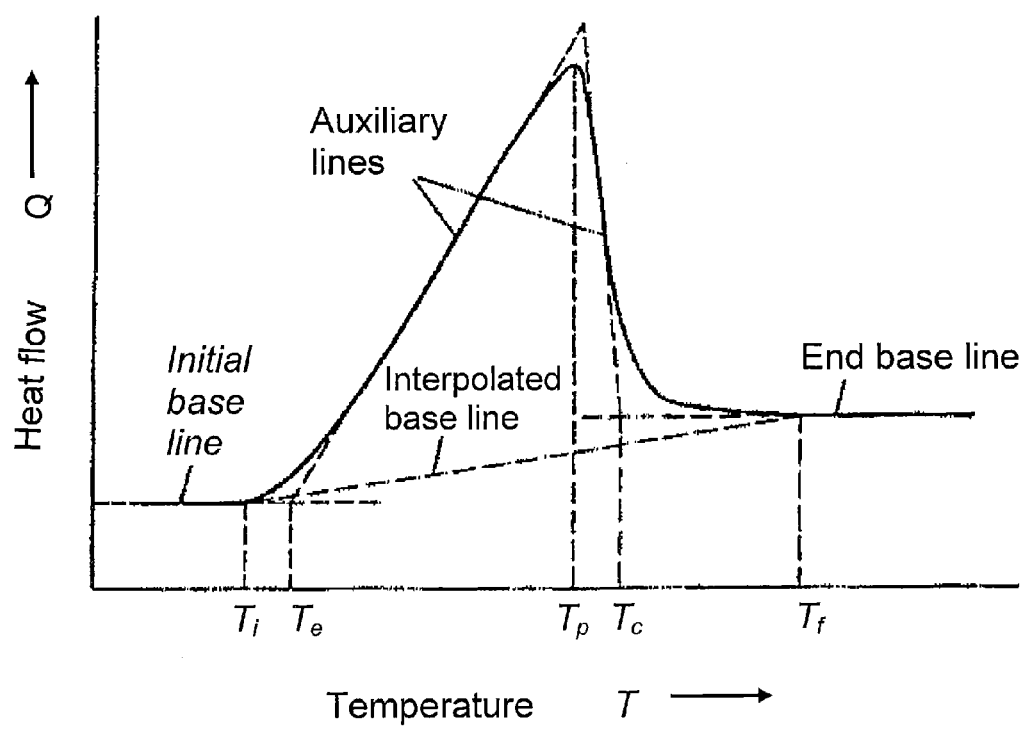
FIG. 4 is a graph of heat flow v. temperature for determination of the eutectic points.

In FIG. 4:

Ti denotes the peak onset temperature; where the measurement curve starts to deviate from the extrapolated initial base line Te denotes the extrapolated peak onset temperature; where the auxiliary line through the ascending peak flank intersects the extrapolated initial base line Tp denotes the peak maximum temperature; where the maximum of the differences between the measurement curve and interpolated base line lies (this is not necessarily the absolute maximum of the measurement curve)

Tc denotes the extrapolated peak end temperature; where the auxiliary line through the descending peak flank intersects the extrapolated end base line Tf denotes the peak end temperature; where the measurement curve reaches the extrapolated end base line again In practice, the base line is interpolated between the peak onset temperature and peak end temperature by various methods (see DIN 51007). For the definition of the extrapolated peak onset and peak end temperature, in most cases a base line interpolated linearly between the peak onset and peak end can be used with sufficient accuracy. The auxiliary lines are laid through the (almost) linear part of the two peak flanks either as inflectional tangents or as regression lines. The differentiation between the two methods is of no significance in (calibrating) practice, since the differences which result are much smaller than the repetition scatters of the measurements. The melting peak is conventionally characterized by the extrapolated peak onset temperature.

Determination of the Phase Diagram of a Three-Component Mixture

Figure 5A:
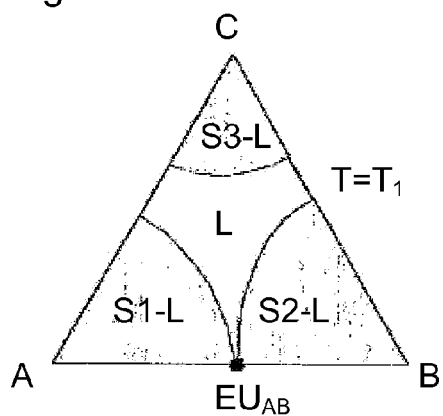
FIG. 5a shows a planar isothermal section through a three-dimensional triangular diagram for determining the eutectic points.
Figure 5B:
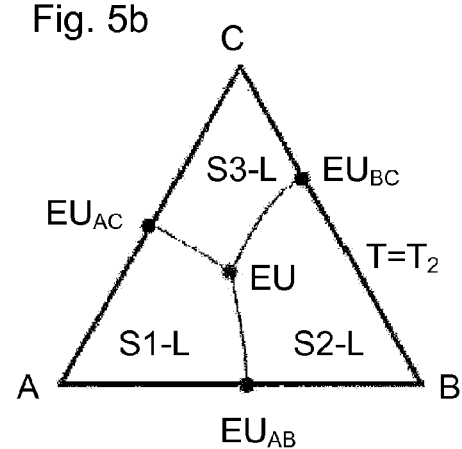
FIG. 5b shows a corresponding plan view of the phase diagram with the triple eutectic point.
Figure 6:
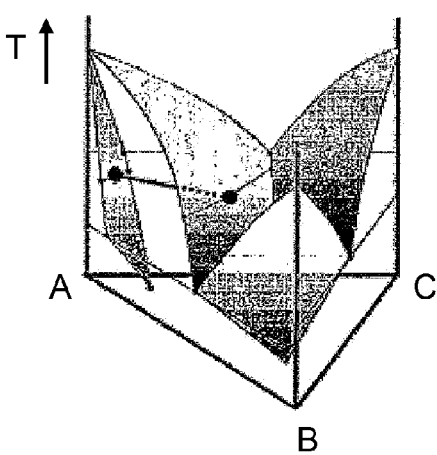
FIG. 6 shows a three-dimensional representation for the determination of the eutectic points.

After the melting points or the melting ranges, i.e. the two-phase ranges, have been measured for various mixtures of a three-component system, these can be plotted in a three-dimensional triangular diagram. This can be visualized on the basis of appropriate evaluation software, e.g. Windows Excel®. The resulting areas of the melting points measured generate so-called eutectic troughs in the eutectic system, which intersect at a defined point, the so-called triple eutectic. FIG. 5*a* shows a planar isothermal section through a three-dimensional triangular diagram. FIG. 5*b* shows a corresponding plan view of the phase diagram with the triple eutectic. FIG. 6 shows a three-dimensional representation.

Determination of the Retention

The retention, called the CRC, is determined in accordance with ERT 441.2-02, where "ERT" stands for "EDANA recommended test" and "EDANA" stands for European Disposables and Nonwovens Association".

Determination of the Absorption Against Pressure

The absorption against a pressure of 0.7 psi, called the AAP, is determined in accordance with ERT 442.2-02.

Determination of the Particle Size

The particle sizes are determined in the present case in accordance with ERT 420.2-02, the sieves stated here being used.

Determination of the Phase Composition

The phase compositions during the crystallization are determined by HPLC and are stated in %.

LIST OF REFERENCE SYMBOLS

1 Feed for biomass
2 Synthesizing unit
3 Outlet for a fermentation solution
4 Killing unit
5 Outlet for a fermentation solution containing killed microorganisms
6 Filtration unit
7 Discharge for solids separated off
8 Outlet for a fermentation solution freed from solids
9 Dehydration stage
   90 Membrane/filter
   91 First reaction vessel
   92 Discharge line for aqueous phase containing at least partly reacted hydroxypropionic acid
   93 Second reaction vessel constructed as a distillation device
   94 Discharge for water
   95 Bottom product containing water, unreacted hydroxypropionic acid and acrylic acid
   96 Feed line for carbon dioxide
10 Outlet for an aqueous phase containing acrylic acid, water and optionally unreacted hydroxypropionic acid
11 Further device constituents, for example
   111 Further filtration units
   112 Protonation means
   113 Adsorption means
   114 Dewatering units
12 Feed line for an aqueous phase containing acrylic acid, water and optionally unreacted hydroxypropionic acid
13 Purification unit
   131 First crystallization device
   132 Discharge line for the crystal suspension obtained in the first crystallization device
   133 First separating region
   134 Melting unit for melting at least a part of the crystals obtained in the first crystallization device
   135 Conveying element, e.g. pump 136 Discharge line for the crystals separated off from the mother liquor in the first separating region and essentially containing water and acrylic acid
137 Melting unit
138 Discharge line for the crystal melt obtained in the melting unit
139 Second crystallization device
1310 Discharge line for the crystal suspension obtained in the second crystallization device
1311 Discharge for the crystals obtained in the second separating region and essentially containing water
1312 Second separating region
1313 Discharge line for the mother liquor separated off from the crystals in the second separating region
1314 Third crystallization device
1315 Discharge line for the crystal suspension obtained in the third crystallization device
1316 Third separating region
1317 Melting unit for melting at least a part of the crystals obtained in the third crystallization device
1318 Conveying element, e.g. pump
1319 Discharge line for the mother liquor separated off in the first separating region
14 Discharge line for purified acrylic acid

The invention claimed is:

1. A process for the preparation of a superabsorbent polymer comprising the steps of:
   I) preparing acrylic acid wherein the acrylic acid is made from a fluid F1 containing a hydroxypropionic acid wherein said fluid F1 is obtained by a process comprising the process steps of i) preparation of hydroxypropionic acid from carbohydrates to give an aqueous phase containing hydroxypropionic acid and solids including microorganisms, and ii) separating off of the solids from said aqueous phase, wherein the hydroxypropionic acid is selected from 2-hydroxypropionic acid or 3-hydroxypropionic acid, wherein the process of preparing acrylic acid comprises the process steps:
      (a1) provision of said fluid F1 containing a hydroxypropionic acid;
   wherein said fluid F1 is aqueous, and has a composition comprising
      (C1-1) from about 5 to about 20 wt. % of hydroxypropionic acid, salts thereof, or mixtures thereof,
      (C1-2) from about 0.1 to about 5 wt. % of inorganic salts,
      (C1-3) from about 0.1 to about 30 wt. % of organic compounds which differ from hydroxypropionic acid,
      (C1-4) from 0 to about 50 wt. % of solids, and
      (C1-5) from about 20 to about 90 wt. % of water,
   wherein the sum of components (C1-1) to (C1-5) is 100 wt. %;
      (a2) dehydration of said hydroxypropionic acid to give a fluid F2 containing acrylic acid wherein the dehydration comprises a reactive distillation and the dehydration is carried out in a $CO_2$ atmosphere, or an inorganic acid, or both; and
      (a3) purification of said fluid F2 containing acrylic acid by crystallization to give a purified acrylic acid phase wherein said purified acrylic acid phase comprises acrylic acid having a purity of at least 70 wt. %; and
   II) polymerizing the acrylic acid of I) in the presence of a crosslinker and a neutralization agent to form a superabsorbent polymer.

2. The process according to claim 1, wherein said hydroxypropionic acid is 3-hydroxypropionic acid.

3. The process according to claim 2, wherein said dehydration is carried out in at least two reactors, comprising the following process steps:
   i) heating of said fluid F1 in at least one first reactor in the presence of a homogeneous or heterogeneous catalyst to give a first aqueous fluid containing acrylic acid under a pressure $\Pi 1$;
   ii) introduction of said first aqueous fluid into a further reactor; and
   iii) heating of said first aqueous fluid introduced into said further reactor in the presence of a catalyst under a pressure $\Pi 2$ to give said fluid F2;
   wherein said pressure $\Pi 2$ and said pressure $\Pi 1$ are not equal.

4. The process according to claim 3, wherein said pressure $\Pi 2$ is lower than said pressure $\Pi 1$.

5. The process according to claim 2, wherein said crystallization is selected from the group consisting of a suspension crystallization or a layer crystallization.

6. The process according to claim 2, further comprising cooling said fluid F1 to a maximum to the temperature of the triple eutectic point of a composition of acrylic acid, water and 3-hydroxypropionic acid.

7. The process according to claim 2, wherein process step (a3) comprises obtaining a first crystal phase;
   wherein said first crystal phase comprises:
      i) at least about 5 wt. % of acrylic acid,
      ii) at least about 40 wt. % of water, and
      iii) at most about 10 wt. % of 3-hydroxypropionic acid.

8. The process according to claim 2, wherein the purification is carried out by and at least two-stage crystallization.

9. The process according to claim 2, wherein process step (a3) comprises the following process steps:
   (a3-1) crystallization of said fluid F2 in a first crystallization stage to give a crystal phase K1 and a mother liquor M1, wherein said crystal phase K1 comprises:
      i) from about 5 to about 60 wt. % of acrylic acid,
      ii) from 39.9 to about 95 wt. % of water, and
      iii) from about 0.1 to about 10 wt. % of by-products which differ from water and acrylic acid,
      and wherein the sum of the amounts by weight of acrylic acid, water and by-products is 100 wt. %,
   (a3-2) separating off of said crystal phase K1 from said mother liquor M1,
   (a3-3) melting of said crystal phase K1 from said first crystallization stage,
   (a3-4) renewed crystallization of said melted crystal phase K1 in a second crystallization stage to give a crystal phase K2 and a mother liquor M2, wherein said crystal phase K2 comprises:
      i) from about 8 to about 35 wt. % of acrylic acid,
      ii) from about 60 to about 90 wt. % of water, and
      iii) from about 2 to about 5 wt. % of by-products which differ from water and acrylic acid,
      wherein the sum of the amounts by weight of acrylic acid, water and by-products is 100 wt. %,
   (a3-5) separating off of said crystal phase K2 from said mother liquor M2,
   (a3-6) crystallization of said mother liquor M2 in a third crystallization stage to give a crystal phase K3 and a mother liquor M3, wherein said crystal phase K3 comprises:
      i) from about 25 to about 55 wt. % of acrylic acid,
      ii) from 44.5 to about 70 wt. % of water, and
      iii) from about 0.5 to about 5 wt. % of by-products which differ from water and acrylic acid,
      wherein the sum of the amounts by weight of acrylic acid, water and by-products is 100 wt. %, and (a3-7) separating off of said crystal phase K3 from said mother liquor M3, a purified phase containing acrylic acid crystals being obtained.

10. The process according to claim 9, wherein the mother liquor obtained in process step (a3-2) is fed back into step (a1).

11. The process according to claim 2, wherein said purified acrylic acid phase has a purity of at least about 40% with respect to the acrylic acid.

12. The process according to claim 2, wherein said 3-hydroxypropionic acid in said fluid F1 or the acrylic acid in said fluid F2 is converted into its protonated form by the addition of acids before carrying out at least one of process steps (a2) or (a3).

13. The process according to claim 1, wherein said hydroxypropionic acid is 2-hydroxypropionic acid.

14. The process according to claim 13, wherein said dehydration is carried out in at least two reactors, comprising the following process steps:
   i) heating of said fluid F1 in at least one first reactor in the presence of a homogeneous or heterogeneous catalyst to give a first aqueous fluid containing acrylic acid under a pressure Π1;
   ii) introduction of said first aqueous fluid into a further reactor; and
   iii) heating of said first aqueous fluid introduced into said further reactor in the presence of a catalyst under a pressure Π2 to give said fluid F2;
wherein said pressure Π2 and said pressure Π1 are not equal.

15. The process according to claim 14, wherein said pressure Π2 is lower than said pressure Π1.

16. The process according to claim 13, wherein said crystallization is selected from the group consisting of a suspension crystallization or a layer crystallization.

17. The process according to claim 13, further comprising cooling said fluid F1 to a maximum to the temperature of the triple eutectic point of a composition of acrylic acid, water and 2-hydroxypropionic acid.

18. The process according to claim 13, wherein process step (a3) comprises obtaining a first crystal phase;
   wherein said first crystal phase comprises:
   i) at least about 5 wt. % of acrylic acid,
   ii) at least about 40 wt. % of water, and
   iii) at most about 10 wt. % of 2-hydroxypropionic acid.

19. The process according to claim 13, wherein the purification is carried out by and at least two-stage crystallization.

20. The process according to claim 13, wherein process step (a3) comprises the following process steps:

(a3-1) crystallization of said fluid F2 in a first crystallization stage to give a crystal phase K1 and a mother liquor M1, wherein said crystal phase K1 comprises:
   i) from about 5 to about 60 wt. % of acrylic acid,
   ii) from 39.9 to about 95 wt. % of water, and
   iii) from about 0.1 to about 10 wt. % of by-products which differ from water and acrylic acid,
   and wherein the sum of the amounts by weight of acrylic acid, water and by-products is 100 wt. %, (a3-2) separating off of said crystal phase K1 from said mother liquor M1, (a3-3) melting of said crystal phase K1 from said first crystallization stage, (a3-4) renewed crystallization of said melted crystal phase K1 in a second crystallization stage to give a crystal phase K2 and a mother liquor M2, wherein said crystal phase K2 comprises:
   i) from about 8 to about 35 wt. % of acrylic acid,
   ii) from about 60 to about 90 wt. % of water, and
   iii) from about 2 to about 5 wt. % of by-products which differ from water and acrylic acid,
   wherein the sum of the amounts by weight of acrylic acid, water and by-products is 100 wt. %, (a3-5) separating off of said crystal phase K2 from said mother liquor M2, (a3-6) crystallization of said mother liquor M2 in a third crystallization stage to give a crystal phase K3 and a mother liquor M3, wherein said crystal phase K3 comprises:
   i) from about 25 to about 55 wt. % of acrylic acid,
   ii) from 44.5 to about 70 wt. % of water, and
   iii) from about 0.5 to about 5 wt. % of by-products which differ from water and acrylic acid,
   wherein the sum of the amounts by weight of acrylic acid, water and by-products is 100 wt. %, and (a3-7) separating off of said crystal phase K3 from said mother liquor M3, a purified phase containing acrylic acid crystals being obtained.

21. The process according to claim 20, wherein the mother liquor obtained in process step (a3-2) is fed back into step (a1).

22. The process according to claim 13, wherein said purified acrylic acid phase has a purity of at least about 40% with respect to the acrylic acid.

23. The process according to claim 13, wherein said hydroxypropionic acid in said fluid F1 or the acrylic acid in said fluid F2 is converted into its protonated form by the addition of acids before carrying out at least one of process steps (a2) or (a3).

* * * * *